US010441613B2

(12) United States Patent
Kaneda et al.

(10) Patent No.: US 10,441,613 B2
(45) Date of Patent: Oct. 15, 2019

(54) ANTI-CANCER AGENT COMPRISING HVJ-E AND CXCL2

(71) Applicants: OSAKA UNIVERSITY, Suita-shi, Osaka (JP); GenomIdea Inc., Osaka (JP)

(72) Inventors: Yasufumi Kaneda, Suita (JP); Toshihiro Nakajima, Ikeda (JP)

(73) Assignees: OSAKA UNIVERSITY, Suita (JP); GenomIdea Inc., Osaka (JP)

( * ) Notice: Subject to any disclaimer, the term of this patent is extended or adjusted under 35 U.S.C. 154(b) by 0 days.

(21) Appl. No.: 15/754,687

(22) PCT Filed: Aug. 23, 2016

(86) PCT No.: PCT/JP2016/074464
§ 371 (c)(1),
(2) Date: Feb. 23, 2018

(87) PCT Pub. No.: WO2017/033912
PCT Pub. Date: Mar. 2, 2017

(65) Prior Publication Data
US 2018/0243355 A1 Aug. 30, 2018

(30) Foreign Application Priority Data
Aug. 24, 2015 (JP) ................................ 2015-164600

(51) Int. Cl.
| | | |
|---|---|---|
| *A61K 39/00* | (2006.01) | |
| *A61K 48/00* | (2006.01) | |
| *C12Q 1/68* | (2018.01) | |
| *A61K 38/00* | (2006.01) | |
| *A61K 35/76* | (2015.01) | |
| *A61K 38/19* | (2006.01) | |
| *A61K 45/00* | (2006.01) | |
| *A61K 31/7088* | (2006.01) | |
| *A61K 31/713* | (2006.01) | |
| *A61K 31/739* | (2006.01) | |
| *A61P 35/00* | (2006.01) | |
| *C12N 7/00* | (2006.01) | |

(52) U.S. Cl.
CPC .......... *A61K 35/76* (2013.01); *A61K 31/7088* (2013.01); *A61K 31/713* (2013.01); *A61K 31/739* (2013.01); *A61K 38/19* (2013.01); *A61K 38/195* (2013.01); *A61K 45/00* (2013.01); *A61K 48/00* (2013.01); *A61P 35/00* (2018.01); *C12N 7/00* (2013.01); *C12N 2760/18833* (2013.01); *C12N 2760/18871* (2013.01)

(58) Field of Classification Search
CPC .............. A61K 2300/00; A61K 48/005; C12Q 1/6886; C12Q 2600/158; G01N 33/57484
See application file for complete search history.

(56) References Cited

PUBLICATIONS

Kawaguchi, Yoshifumi, et al., "Efficient eradication of hormone-resistant human prostate cancers by inactivated Sendai virus particle", International journal of cancer, 2009, 124(10):2478-2487.*
Nakahara, Masaki, et al., Effect of Lipopolysaccharide from Proteus mirabilis, alone or with Antitumor Agents, against Experimental Animal Tumours, Agricultural and Biological Chemistry, 1976,40(6):1201-1208.*
Tsutsumi, Y., et al., Molecular design of hybrid tumour necrosis factor alpha with polyethylene glycol increases its anti-tumour potency, British journal of cancer, 1995, 71(5), 963-8.*
Mickey, Don D., et al., Effects of the immunomodulator PSK on growth of human prostate adenocarcinoma in immunodeficient mice, International journal of immunopharmacology,1989,11(7):pdf Abstract.*
Besch et al., "Proapoptotic signaling induced by RIG-I and MDA-5 results in type I interferon-independent apoptosis in human melanoma cells," *J. Clin. Invest.*, 119(8): 2399-2411 (2009).
Kawaguchi et al., "Efficient eradication of hormone-resistant human prostate cancers by inactivated Sendai virus particle," *Int. J. Cancer*, 124(1): 2478-2487 (2009).
Kurooka et al., "Inactivated Sendai Virus Particles Eradicate Tumors by Inducing Immune Responses through Blocking Regulatory T Cells," *Cancer Res.*, 67(1): 227-236 (2007).
Matsushima-Miyagi et al., "TRAIL and Noxa are Selectively Upregulated in Prostate Cancer Cells Downstream of the RIG-I/MAVS Signaling Pathway by Nonreplicating Sendai Virus Particles," *Clin. Cancer Res.*, 18(22): 6271-6283 (2012).
Nakahara et al., "Effect of Lipopolysaccharide from *Proteus mirabilis*, alone or with Antitumor Agents, against Experimental Animal Tumors," *Agr. Biol. Chem.*, 40(6): 1201-1208 (1976).
Nomura et al., "Accumulation of Cytosolic Calcium Induces Necroptotic Cell Death in Human Neuroblastoma," *Cancer Res.*, 74(4): 1056-1066 (2014).
Suzuki et al., "Sendai virus F glycoprotein induces IL-6 production in dendritic cells in a fusion-independent manner," *FEBS Lett.*, 582(9): 1325-1329 (2008).
Tsutsumi et al., "Molecular design of hybrid tumour necrosis factor alpha with polyethylene glycol increases its anti-tumour potency," *Br. J. Cancer*, 71(5): 963-968 (1995).
Japanese Patent Office, International Search Report in International Patent Application No. PCT/JP2016/074464 (dated Nov. 15, 2016), English translation.
Buenestado et al., "Roflumilast Inhibits Lipopolysaccharide-Induced Tumor Necrosis Factor-α and Chemokine Production by Human Lung Parenchyma," *PLoS One*, 8(9): e74640 (2013).

(Continued)

*Primary Examiner* — Barry A Chestnut
(74) *Attorney, Agent, or Firm* — Leydig, Voit & Mayer, Ltd.

(57) ABSTRACT

The present invention provides, as a new anti-cancer agent obtained by combining HVJ-E and a molecule synergistically acting therewith, an anti-cancer agent containing the following (1) and (2):
(1) HVJ-E (hemagglutinating virus of Japan envelope),
(2) CXCL2, a nucleic acid comprising a base sequence encoding CXCL2 or a CXCL2 expression inducing agent.

12 Claims, 14 Drawing Sheets

Specification includes a Sequence Listing.

(56) References Cited

PUBLICATIONS

Chang et al., "Virus-stimulated neutrophils in the tumor microenvironment enhance T cell-mediated anti-tumor immunity," *Oncotarget*, 7(27): 42195-42207 (2016).

Fridlender et al., "Polarization of Tumor-Associated Neutrophil (TAN) Phenotype by TGF-β: 'N1' versus 'N2' TAN," *Cancer Cell.*, 16(3): 183-194 (2009).

Fujimura et al., "Inhibitory effect of the polyinosinic-polycytidylic acid/cationic liposome on the progression of murine B16F10 melanoma," *Eur. J. Immunol.*, 36(12): 3371-3380 (2006).

Jiang et al., "IFN-producing Killer Dendritic Cells Contribute to the Inhibitory Effect of Poly I:C on the Progression of Murine Melanoma," *J. Immunother.*, 31(6): 555-562 (2008).

Kearney et al., "Inhibitor of Apoptosis Proteins (IAPs) and Their Antagonists Regulate Spontaneous and Tumor Necrosis Factor (TNF)-induced Proinflammatory Cytokine and Chemokine Production," *J. Biol. Chem.*, 288(7): 4878-4890 (2013).

Nakajima et al., "A Novel Therapy for Melanoma and Prostate Cancer Using a Non-Replicating Sendai Virus Particle (HVJ-E)," *Novel Gene Therapy Approaches*, Chapter 8, pp. 157-181 (2013).

Son et al., "Characteristics of chemokine signatures elicited by EGF and TNF in ovarian cancer cells," *J. Inflamm.*, 10: 25 (2013).

European Patent Office, Supplementary European Search Report in European Patent Application No. 16839259 (dated Feb. 19, 2019).

\* cited by examiner

SEQUENCE LISTING

<160> NUMBER OF SEQ ID NOS: 20

<210> SEQ ID NO 1
<211> LENGTH: 324
<212> TYPE: DNA
<213> ORGANISM: Homo sapiens

```
<220> FEATURE:
<221> NAME/KEY: CDS
<222> LOCATION: (1)..(324)

<400> SEQUENCE: 1 atg gcc cgc gcc acg ctc tcc gcc gcc ccc agc aat ccc cgg ctc ctg     48
Met Ala Arg Ala Thr Leu Ser Ala Ala Pro Ser Asn Pro Arg Leu Leu
1               5                   10                  15 cgg gtg gcg ctg ctg ctc ctg ctc gtg gcc gcc agc cgg cgc gca         96
Arg Val Ala Leu Leu Leu Leu Leu Val Ala Ala Ser Arg Arg Ala
            20                  25                  30 gca gga gcg ccc ctg gcc act gaa ctg cgc tgc cag tgc ttg cag acc    144
Ala Gly Ala Pro Leu Ala Thr Glu Leu Arg Cys Gln Cys Leu Gln Thr
        35                  40                  45 ctg cag gga att cac ctc aag aac atc caa agt gtg aag gtg aag tcc    192
Leu Gln Gly Ile His Leu Lys Asn Ile Gln Ser Val Lys Val Lys Ser
50                  55                  60 ccc gga ccc cac tgc gcc caa acc gaa gtc ata gcc aca ctc aag aat    240
Pro Gly Pro His Cys Ala Gln Thr Glu Val Ile Ala Thr Leu Lys Asn
65                  70                  75                  80 ggg cag aaa gct tgt ctc aac ccc gca tcg ccc atg gtt aag aaa atc    288
Gly Gln Lys Ala Cys Leu Asn Pro Ala Ser Pro Met Val Lys Lys Ile
                85                  90                  95 atc gaa aag atg ctg aaa aat ggc aaa tcc aac tga                    324
Ile Glu Lys Met Leu Lys Asn Gly Lys Ser Asn
                100                 105

<210> SEQ ID NO 2
<211> LENGTH: 107
<212> TYPE: PRT
<213> ORGANISM: Homo sapiens

<400> SEQUENCE: 2

Met Ala Arg Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
            20                  25                  30

Ala Gly Ala Pro Leu Ala Thr Glu Leu Arg Cys Gln Cys Leu Gln Thr
        35                  40                  45

Leu Gln Gly Ile His Leu Lys Asn Ile Gln Ser Val Lys Val Lys Ser
    50                  55                  60

Pro Gly Pro His Cys Ala Gln Thr Glu Val Ile Ala Thr Leu Lys Asn
65                  70                  75                  80

Gly Gln Lys Ala Cys Leu Asn Pro Ala Ser Pro Met Val Lys Lys Ile
                85                  90                  95

Ile Glu Lys Met Leu Lys Asn Gly Lys Ser Asn
                100                 105

<210> SEQ ID NO 3
<211> LENGTH: 28
<212> TYPE: DNA
<213> ORGANISM: Artificial Sequence
<220> FEATURE:
<223> OTHER INFORMATION: Synthetic sequence - primer

<400> SEQUENCE: 3
aagcttgcca ccatggcccc tcccacct                                      28

<210> SEQ ID NO 4
<211> LENGTH: 25
<212> TYPE: DNA
```

<213> ORGANISM: Artificial Sequence
<220> FEATURE:
<223> OTHER INFORMATION: Synthetic sequence - primer

<400> SEQUENCE: 4
ctcgagtcag ttagccttgc ctttg    25

<210> SEQ ID NO 5
<211> LENGTH: 21
<212> TYPE: DNA
<213> ORGANISM: Artificial Sequence
<220> FEATURE:
<223> OTHER INFORMATION: Synthetic sequence - primer

<400> SEQUENCE: 5
tggactctca cagaagcaaa g    21

<210> SEQ ID NO 6
<211> LENGTH: 21
<212> TYPE: DNA
<213> ORGANISM: Artificial Sequence
<220> FEATURE:
<223> OTHER INFORMATION: Synthetic sequence - primer

<400> SEQUENCE: 6
gcagaggtct tccttccaac a    21

<210> SEQ ID NO 7
<211> LENGTH: 20
<212> TYPE: DNA
<213> ORGANISM: Artificial Sequence
<220> FEATURE:
<223> OTHER INFORMATION: Synthetic sequence - primer

<400> SEQUENCE: 7
gactccagcc acactccaac    20

<210> SEQ ID NO 8
<211> LENGTH: 18
<212> TYPE: DNA
<213> ORGANISM: Artificial Sequence
<220> FEATURE:
<223> OTHER INFORMATION: Synthetic sequence - primer

<400> SEQUENCE: 8
tgacagcgca gctcattg    18

<210> SEQ ID NO 9
<211> LENGTH: 26
<212> TYPE: DNA
<213> ORGANISM: Artificial Sequence
<220> FEATURE:
<223> OTHER INFORMATION: Synthetic sequence - primer

<400> SEQUENCE: 9
aaaatcatcc aaaagatact gaacaa    26

<210> SEQ ID NO 10
<211> LENGTH: 20
<212> TYPE: DNA
<213> ORGANISM: Artificial Sequence
<220> FEATURE:
<223> OTHER INFORMATION: Synthetic sequence - primer

<400> SEQUENCE: 10
ctttggttct tccgttgagg    20

```
<210> SEQ ID NO 11
<211> LENGTH: 18
<212> TYPE: DNA
<213> ORGANISM: Artificial Sequence
<220> FEATURE:
<223> OTHER INFORMATION: Synthetic sequence - primer

<400> SEQUENCE: 11 ggaggggtt gaggtgtt                                                    18

<210> SEQ ID NO 12
<211> LENGTH: 24
<212> TYPE: DNA
<213> ORGANISM: Artificial Sequence
<220> FEATURE:
<223> OTHER INFORMATION: Synthetic sequence - primer

<400> SEQUENCE: 12
gtgtgcactt ttattggtct caag                                            24

<210> SEQ ID NO 13
<211> LENGTH: 18
<212> TYPE: DNA
<213> ORGANISM: Artificial Sequence
<220> FEATURE:
<223> OTHER INFORMATION: Synthetic sequence - primer

<400> SEQUENCE: 13
gtggcgggaa agttcctg                                                   18

<210> SEQ ID NO 14
<211> LENGTH: 23
<212> TYPE: DNA
<213> ORGANISM: Artificial Sequence
<220> FEATURE:
<223> OTHER INFORMATION: Synthetic sequence - primer

<400> SEQUENCE: 14
cgtcttgcag gtcatcttag gag                                             23

<210> SEQ ID NO 15
<211> LENGTH: 25
<212> TYPE: DNA
<213> ORGANISM: Artificial Sequence
<220> FEATURE:
<223> OTHER INFORMATION: Synthetic sequence - primer

<400> SEQUENCE: 15
aacgggaaga catacttctt cataa                                           25

<210> SEQ ID NO 16
<211> LENGTH: 20
<212> TYPE: DNA
<213> ORGANISM: Artificial Sequence
<220> FEATURE:
<223> OTHER INFORMATION: Synthetic sequence - primer

<400> SEQUENCE: 16
gggtccatgg atcttctttg                                                 20

<210> SEQ ID NO 17
<211> LENGTH: 21
<212> TYPE: DNA
<213> ORGANISM: Artificial Sequence
<220> FEATURE:
```

```
<223> OTHER INFORMATION: Synthetic sequence - primer

<400> SEQUENCE: 17
cacagccctc tccatcaact a                                              21

<210> SEQ ID NO 18
<211> LENGTH: 20
<212> TYPE: DNA
<213> ORGANISM: Artificial Sequence
<220> FEATURE:
<223> OTHER INFORMATION: Synthetic sequence - primer

<400> SEQUENCE: 18
catttccgaa tgttcgtcct                                                20

<210> SEQ ID NO 19
<211> LENGTH: 20
<212> TYPE: DNA
<213> ORGANISM: Artificial Sequence
<220> FEATURE:
<223> OTHER INFORMATION: Synthetic sequence - primer

<400> SEQUENCE: 19
tggagcaaca tgtggaactc                                                20

<210> SEQ ID NO 20
<211> LENGTH: 18
<212> TYPE: DNA
<213> ORGANISM: Artificial Sequence
<220> FEATURE:
<223> OTHER INFORMATION: Synthetic sequence - primer

<400> SEQUENCE: 20
gtcagcagcc ggttacca                                                  18
```

ANTI-CANCER AGENT COMPRISING HVJ-E AND CXCL2

CROSS-REFERENCE TO RELATED APPLICATIONS

This patent application is the U.S. national phase of International Patent Application No. PCT/JP2016/074464, filed Aug. 23, 2016, which claims the benefit of Japanese Patent Application No. 2015-164600, filed on Aug. 24, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 6,597 bytes ASCII (Text) file named "738421SequenceListing.txt," created Feb. 22, 2018

TECHNICAL FIELD

The present invention relates to an anti-cancer agent containing HVJ-E (hemagglutinating virus of Japan envelope) and CXCL2 (or a nucleic acid containing a base sequence encoding CXCL2, a CXCL2 production inducing agent). The present invention also relates to an N1 type neutrophil inducing agent containing HVJ-E and CXCL2 (or a nucleic acid containing a base sequence encoding CXCL2, a CXCL2 production inducing agent).

BACKGROUND ART

Innate immunity is an essential defense system of vertebrates against invasion of pathogenic factors and, for example, Toll-like receptors (TLRs), retinoic acid-inducible gene I (RIG-I)-like receptors (RLRs), Nod-like receptors, cytosolic DNA receptors, cell surface C-type lectin receptors and the like play a major role. Of the above-mentioned receptors, TLRs are also known to have a role responsible for antitumor immunity, and clinical attempts to treat cancer patients are ongoing using BCG as TLR2/4 agonist, poly I:C as TLR3 agonist, monophosphoryl lipid A (MLA) as TLR4 agonist, Imiquimod (synthetic imidazoquinoline) as TLR7 agonist, SD-101 (phosphorothioate CpG ODN) as TLR9 agonist and the like.

On the other hand, the involvement of RLRs, from among the above-mentioned receptors, in the antitumor immunity has scarcely been reported; however, it has been reported that synthetic DNA could induce interferon independent apoptosis in human melanoma via RIG-I and MDA5 activation (non-patent document 1). The inventors have also reported that completely inactivated HVJ (hemagglutinating virus of Japan) has plural antitumor activities including antitumor immunity and induction of cancer cell-specific apoptosis (non-patent document 2), and found that virus-derived RNA fragments in HVJ-E are transduced via membrane fusion into the cytoplasm and recognized by RIG-I, and a virus-derived RNA/RIG-I complex activates transcription factors such as NF-κB, IRF-3, IRF-7 via a mitochondria antivirus signal protein (MAVS), activates pro-apoptotic molecules such as TRAIL and NOXA in human cancer cells, but does not activate those in non-cancer cells (non-patent documents 2, 3). The inventors have also found that HVJ-E transiently increases calcium in cytoplasm via membrane fusion and induces necroptosis of caspase8-deficient neuroblastoma cells (non-patent document 4). In addition, the inventors have reported that the function of regulatory T cell is suppressed independently of the membrane fusion by stimulating the production of IL-6 from dendritic cells via interaction of unidentified cell surface receptors on the dendritic cells with F protein of HVJ-E, thus contributing to the activation of antitumor immunity (non-patent documents 5, 6).

As mentioned above, the present inventors have demonstrated that HVJ-E can suppress proliferation of cancer cells by activating various signal transductions. However, it is still unknown how the proliferation suppressive effect of HVJ-E on cancer cells changes when signal transduction via TLRs is simultaneously activated.

DOCUMENT LIST

Non-Patent Documents non-patent document 1: Besch R, Poeck H, Hohenauer T, Senft D, Hacker G, Berking C, Hornung V, Endres S, Ruzicka T, Rothenfusser S, Hartmann G. 2009. Proapoptotic signaling induced by RIG-I and MDA-5 results in type I interferon-independent apoptosis in human melanoma cells. J. Clin. Invest. 119: 2399-2411.

non-patent document 2: Kawaguchi Y, Mitamoto Y, Inoue T, Kaneda Y. Efficient eradication of hormone-resistant human prostate cancers by inactivated Sendai virus particle. Int. J. Cancer 2009. 124: 2478-87.

non-patent document 3: Matsushima-Miyagi T., Hatano K., Nomura M., Li-Wen L., Nishikawa T., Saga K., Shimbo T, Kaneda Y. TRAIL and Noxa are selectively up-regulated in prostate cancer cells downstream of the RIG-I/ MAVS signaling pathway by non-replicating Sendai virus particles. Clinical Cancer Research, 18, 6271-83, 2012.

non-patent document 4: Nomura M, Ueno A, Saga K, Fukuzawa M, Kaneda Y. Accumulation of cytosolic calcium induces necroptotic cell death in human neuroblastoma. Cancer Res. 74, 1056-1066, 2014.

non-patent document 5: Suzuki H, Kurooka M, Hiroaki Y, Fujiyoshi Y, Kaneda Y. Sendai virus F glycoprotein induces IL-6 production in dendritic cells in a fusion-independent manner. FEES Letter, 2008. 582: 1325-29.

non-patent document 6: Kurooka M Kaneda Y. Inactivated Sendai virus particles eradicate tumors by inducing immune responses through blocking regulatory T cells. Cancer Research, 67, 227-236, 2007.

SUMMARY OF THE INVENTION

Problems to be Solved by the Invention

An object of the present invention is to provide a new anti-cancer agent having a high proliferation suppressive effect on cancer cells, which agent is obtained by confirming whether an antitumor effect by HVJ-E cooperatively acts with activation of signal transduction via TLRs and more strongly suppresses proliferation of cancer cells and, based on the results thereof, combining a molecule that synergistically acts with HVJ-E.

Means of Solving the Problems

In an attempt to solve the aforementioned problems, the present inventors administered HVJ-E and a TLR3 agonist Poly I:C in combination to tumor-bearing mice. As a result, it was confirmed that HVJ-E cooperatively acts with activation of signal transduction via TLRs and suppresses proliferation of cancer cells. Furthermore, it was found that a cancer proliferation suppressive effect is high beyond prediction of those of ordinary skill in the art, compared to single administration of HVJ-E or single administration of Poly I:C, respectively. In addition, it was found that Poly I:C induces expression of CXCL2 in tumor and infiltration of neutrophils into tumor. Moreover, neutrophil was converted to N1 type neutrophil by IFN-β whose expression is induced in dendritic cell and the like by HVJ-E, or neutrophil was converted to N1 type neutrophil by HVJ-E itself. It is known that N1 type neutrophil is involved in suppression of cancer proliferation. In addition, it was found that a cancer proliferation suppressive effect is high beyond prediction of those of ordinary skill in the art when HVJ-E and CXCL2 protein or CXCL2 expression vector are administered in combination to tumor-bearing mice, compared to single administration of HVJ-E or single administration of CXCL2, respectively. From The present invention has been completed based on the above findings. That is, the present invention provides

[1] an anti-cancer agent comprising the following (1) and (2):
(1) HVJ-E (hemagglutinating virus of Japan envelope),
(2) CXCL2, a nucleic acid comprising a base sequence encoding CXCL2 or a CXCL2 expression inducing agent;
[2] the anti-cancer agent of [1], wherein the nucleic acid comprising the base sequence encoding CXCL2 is an expression vector comprising a base sequence encoding CXCL2;
[3] the anti-cancer agent of [1] or [2], wherein the nucleic acid comprising a base sequence encoding CXCL2 is encapsulated in HVJ-E;
[4] the anti-cancer agent of [1], wherein the CXCL2 expression inducing agent is selected from the group consisting of synthesized double stranded RNA, Lipopolysaccharide, leukotriene 4, platelet-activating factor (PAF), angiotensin II (Ang II), tumor necrosis factor-α (TNF-α) and Interleukin-17 (IL-17);
[5] the anti-cancer agent of [4], wherein the synthesized double stranded RNA is PolyI:C;
[6] the anti-cancer agent of any one of [1] to [5], wherein the cancer is selected from the group consisting of melanoma, lung cancer, mesothelioma, tongue cancer, esophagus cancer, gastric cancer, liver cancer, large intestine cancer, prostate cancer, kidney cancer, bladder cancer, breast cancer, uterine cancer, ovarian cancer, brain tumor, thyroid cancer, angiosarcoma, osteosarcoma, chondrosarcoma, rhabdomyosarcoma and leiomyosarcoma;
[7] an N1 type neutrophil inducing agent comprising the following (1) and (2):
(1) HVJ-E (hemagglutinating virus of Japan envelope),
(2) CXCL2, a nucleic acid comprising a base sequence encoding CXCL2 or a CXCL2 expression inducing agent;
[8] the N1 type neutrophil inducing agent of [7], wherein the nucleic acid comprising a base sequence encoding CXCL2 is an expression vector comprising a base sequence encoding CXCL2;
[9] the N1 type neutrophil inducing agent of [7] or [8], wherein the nucleic acid comprising a base sequence encoding CXCL2 is encapsulated in HVJ-E;
[10] the N1 type neutrophil inducing agent of [7], wherein the CXCL2 expression inducing agent is selected from the group consisting of synthesized double stranded RNA, Lipopolysaccharide, leukotriene 4, platelet-activating factor (PAF), angiotensin II (Ang II), tumor necrosis factor-α (TNF-α) and Interleukin-17 (IL-17);
[11] the N1 type neutrophil inducing agent of [10], wherein the synthesized double strand is PolyI:C;
[12] a method for the prophylaxis or treatment of cancer, comprising administering an effective amount of a pharmaceutical composition comprising the following (1) and (2) to a subject:
(1) HVJ-E (hemagglutinating virus of Japan envelope),
(2) CXCL2, a nucleic acid comprising a base sequence encoding CXCL2 or a CXCL2 expression inducing agent;
[13] a method of inducing an N1 type neutrophil, comprising administering an effective amount a pharmaceutical composition comprising the following (1) and (2) to a subject:
(1) HVJ-E (hemagglutinating virus of Japan envelope),
(2) CXCL2, a nucleic acid comprising a base sequence encoding CXCL2 or a CXCL2 expression inducing agent;
[14] a pharmaceutical composition comprising the following (1) and (2) for use in the prophylaxis or treatment of cancer:
(1) HVJ-E (hemagglutinating virus of Japan envelope),
(2) CXCL2, a nucleic acid comprising a base sequence encoding CXCL2 or a CXCL2 expression inducing agent;
[15] a pharmaceutical composition comprising the following (1) and (2) for use in the induction of N1 type neutrophil:
(1) HVJ-E (hemagglutinating virus of Japan envelope),
(2) CXCL2, a nucleic acid comprising a base sequence encoding CXCL2 or a CXCL2 expression inducing agent;
[16] use of the following (1) and (2) in the production of an anti-cancer agent:
(1) HVJ-E (hemagglutinating virus of Japan envelope),
(2) CXCL2, a nucleic acid comprising a base sequence encoding CXCL2 or a CXCL2 expression inducing agent;
[17] use of the following (1) and (2) in the production of an N1 type neutrophil inducing agent:
(1) HVJ-E (hemagglutinating virus of Japan envelope),
(2) CXCL2, a nucleic acid comprising a base sequence encoding CXCL2 or a CXCL2 expression inducing agent.

Effect of the Invention the present invention can provide a new anti-cancer agent containing a combination of HVJ-E and CXCL2, a nucleic acid comprising a base sequence encoding CXCL2 or a CXCL2 expression inducing agent as an active ingredient.

DESCRIPTION OF EMBODIMENTS

Figure 1:
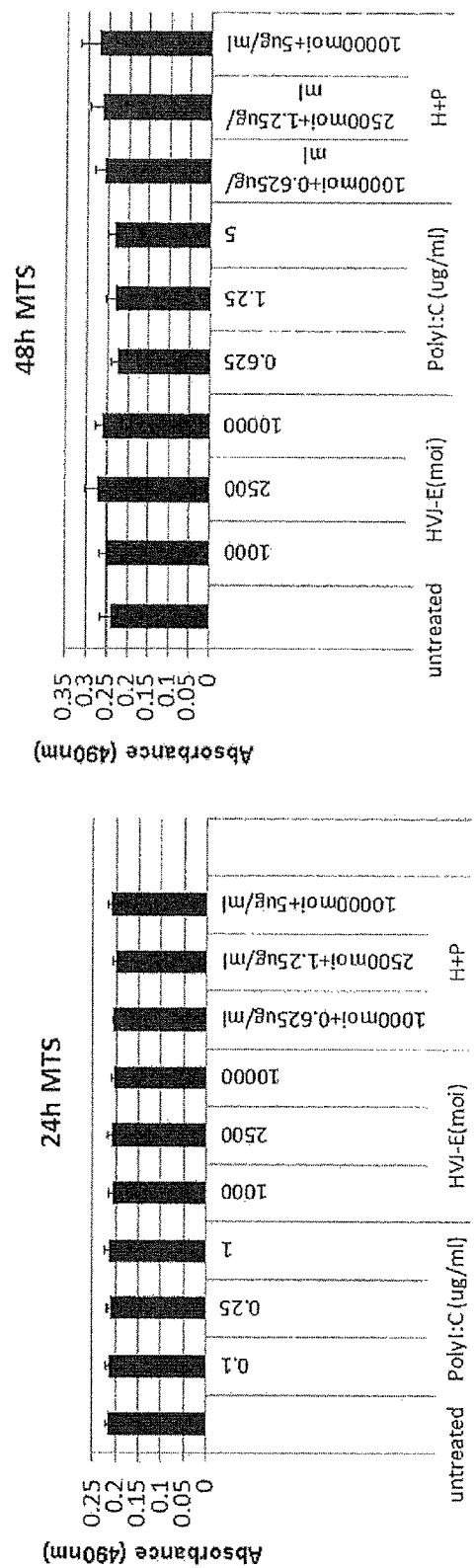
FIG. 1 shows the results of MTS assay when PBS, poly I:C, HVJ-E or HVJ-E+poly I:C (H+P) was used.

The present invention is explained in detail in the following.

The present invention provides an anti-cancer agent comprising the following (1) and (2):
(1) HVJ-E (hemagglutinating virus of Japan envelope),
(2) CXCL2, a nucleic acid comprising a base sequence encoding CXCL2 or a CXCL2 expression inducing agent.

The present invention also provides an N1 type neutrophil inducing agent comprising the following (1) and (2):
(1) HVJ-E (hemagglutinating virus of Japan envelope),
(2) CXCL2, a nucleic acid comprising a base sequence encoding CXCL2 or a CXCL2 expression inducing agent.

In the present invention, Sendai virus envelope (hemagglutinating virus of Japan envelope, hereinafter HVJ-E of the present invention) refers to a virus envelope derived from Sendai virus (hemagglutinating virus of Japan, hereinafter HVJ). HVJ refers to a virus belonging to Paramyxoviridae Genus paramyxovirus and having a cell fusion activity. HVJ particles have, on the surface thereof, an envelope having hemagglutinin and neuraminidase and show polymorphism in diameter 150-300 nm. HVJ has, as a genome, negative-strand RNA of about 15,500 bases in length, has RNA polymerase, is unstable to heat, coagulates almost all kinds of erythrocytes and shows hemolysis. Examples of HVJ used for the preparation of HVJ-E of the present invention include VR-105, VR-907 and the like, and can be purchased from American Type Culture Collection (ATCC). HVJ may be a wild-type virus or a recombinant virus.

HVJ-E of the present invention can be prepared by inactivating RNA of HVJ. Examples of the method for inactivating HVJ for the preparation of HVJ-E of the present invention include UV treatment and alkylation treatment. By the inactivation treatment, the genomic RNA is modified or fragmented within the viral envelope and loses its activity, whereby the replication competence as a virus is lost. A method for preparing HVJ-E of the present invention is specifically described in JP-A-2001-286282 (WO 01/57204), JP-A-2002-065278, WO 03/014338 and the like, and particularly, HVJ-E can be prepared according to the method described in Example 8 and the like of JP-A-2001-286282. The thus-obtained HVJ-E of the present invention having no replication competence can be utilized as a gene transfer vector by encapsulating gene, polynucleotide, oligonucleotide, plasmid and the like. HVJ-E of the present invention may also be a fused particle obtained by fusing a liposome encapsulating gene and protein, and HVJ after previous inactivation of RNA by UV radiation (Sendai virus-liposome).

In the present invention, CXCL2 is a protein comprising the same or substantially the same amino acid sequence as the amino acid sequence shown in SEQ ID NO:2.

CXCL2 may be, for example, a protein isolated and purified from a human cell. It may also be a chemically-synthesized protein or a protein biochemically synthesized in a cell-free translation system. Alternatively, the protein may be a recombinant protein produced from a transformant incorporating a nucleic acid comprising a base sequence that encodes the above-described amino acid sequence.

Substantially the same amino acid sequence as the amino acid sequence shown in SEQ ID NO:2 refers to an amino acid sequence having a homology of about 60% or more, preferably about 70% or more, further preferably about 80% or more, particularly preferably about 90% or more, most preferably about 95% or more, to the amino acid sequence shown in SEQ ID NO:2, and the like. Here, "a homology" means a ratio (%) of identical amino acid residues and similar amino acid residues to all overlapping amino acid residues in the optimal alignment (preferably, the algorithm considers introduction of gaps on one or both sides of the sequence for the best alignment) where two amino acid sequences are aligned using a mathematical algorithm known in the technical field.

Amino acid sequence homology in the present description can be calculated using the homology calculation algorithm NCBI BLAST (National Center for Biotechnology Information Basic Local Alignment Search Tool) under the following conditions (expectancy=10; gaps allowed; matrix=BLOSUM62; filtering=OFF). As examples of other algorithms for determination of amino acid sequence homology, the algorithm described in Karlin et al., Proc. Natl. Acad. Sci. USA, 90:5873-5877 (1993) [the algorithm is incorporated in the NBLAST and XBLAST programs (version 2.0) (Altschul et al., Nucleic Acids Res., 25:3389-3402 (1997))], the algorithm described in Needleman et al., J. Mol. Biol., 48:444-453 (1970) [the algorithm is incorporated in the GAP program in the GCG software package], the algorithm described in Myers and Miller, CABIOS, 4:11-17 (1988) [the algorithm is incorporated in the ALIGN program (version 2.0), which is part of the CGC sequence alignment software package], the algorithm described in Pearson et al., Proc. Natl. Acad. Sci. USA, 85:2444-2448 (1988) [the algorithm is incorporated in the FASTA program in the GCG software package] and the like can be mentioned, which can likewise be used preferably.

More preferably, substantially the same amino acid sequence as the amino acid sequence shown in SEQ ID NO:2 is an amino acid sequence having an identity of about 60% or more, preferably about 70% or more, further preferably about 80% or more, particularly preferably about 90% or more, and most preferably about 95% or more, to the amino acid sequence shown in SEQ ID NO:2.

As a protein comprising substantially the same amino acid sequence as the amino acid sequence shown in SEQ ID NO:2, for example, a protein comprising substantially the same amino acid sequence as the aforementioned amino acid sequence shown in SEQ ID NO:2, and having an activity substantially of the same quality as that of a protein comprising the amino acid sequence shown in SEQ ID NO:2 and the like are preferable. Here, the "activity" refers to, for example, neutrophil-attracting activity and the like. Being "substantially of the same quality" means that the activity thereof is qualitatively (e.g., physiologically or pharmacologically) the same. Therefore, it is preferable that the aforementioned activities be equivalent to each other, but the quantitative factors of these activities, such as the extent of activity (e.g., about 0.1 to about 10 times, preferably about 0.5 to about 2 times) and the molecular weight of the protein, may be different.

The aforementioned activities can be measured by a method known per se such as FACS and the like.

CXCL2 of the present invention is preferably a human CXCL2 protein consisting of the amino acid sequence shown in SEQ ID NO:2.

In the present specification, the protein is described according to the common practice of peptide designation, wherein the left end indicates the N-terminal (amino terminal) and the right end indicates the C-terminal (carboxyl terminal). In CXCL2 of the present invention including a protein comprising the amino acid sequence shown in SEQ ID NO:2, the C-terminal may be any of a carboxyl group (—COOH), carboxylate (—COO$^-$), amide (—CONH$_2$) and ester (—COOR).

Here, as R in the ester, a $C_{1-6}$ alkyl group, for example, methyl, ethyl, n-propyl, isopropyl and n-butyl, a $C_{3-8}$ cycloalkyl group, for example, cyclopentyl and cyclohexyl, a $C_{6-12}$ aryl group, for example, phenyl and α-naphthyl, a phenyl-$C_{1-2}$ alkyl group, for example, benzyl and phenethyl, a $C_{7-14}$ aralkyl group, for example, an α-naphthyl-$C_{1-2}$ alkyl group such as α-naphthylmethyl, a pivaloyloxymethyl group; and the like can be used.

When the CXCL2 of the present invention has a carboxyl group (or carboxylate) at a position other than the C-terminal, a protein wherein the carboxyl group is amidated or esterified is also included in the protein of the present invention. In this case, as the ester, the above-described ester at the C terminal, and the like, for example, are used.

Furthermore, the CXCL2 of in the present invention also includes a protein wherein the amino group of the N-terminal amino acid residue is protected by a protecting group (e.g., $C_{1-6}$ acyl groups such as $C_{1-6}$ alkanoyls such as formyl group and acetyl group, and the like); a protein wherein the glutamine residue that may be produced upon cleavage at the N terminal in vivo has been converted to pyroglutamic acid, a protein wherein a substituent (e.g., —OH, —SH, amino group, imidazole group, indol group, guanidino group and the like) on a side chain of an amino acid in the molecule is protected by an appropriate protecting group (e.g., $C_{1-6}$ acyl groups such as $C_{1-6}$ alkanoyl groups such as formyl group and acetyl group, and the like), a conjugated peptide such as what is called a glycopeptide having a sugar chain bound thereto, and the like.

CXCL2 to be used in the present invention may be in the form of a salt. For example, salts with physiologically acceptable acid (e.g., inorganic acid, organic acid), base (e.g., alkali metal salt) and the like are used, and physiologically acceptable acid addition salts are preferable. Useful salts include, for example, salts with inorganic acids (e.g., hydrochloric acid, phosphoric acid, hydrobromic acid, sulfuric acid) or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

CXCL2 can be produced from a cell of the aforementioned mammals by a protein purification method known per se. To be specific, CXCL2 or a salt thereof can be prepared by homogenizing mammalian cells, removing cell debris by low-speed centrifugation, centrifuging the supernatant at a high speed to precipitate a cellular membrane-comprising fraction, and subjecting the supernatant to chromatography such as reversed-phase chromatography, ion exchange chromatography, affinity chromatography and the like, and the like.

CXCL2 can also be produced according to a publicly known method of peptide synthesis.

The method of peptide synthesis may be any of, for example, a solid phase synthesis process and a liquid phase synthesis process. A desired protein can be produced by condensing a partial peptide or amino acid capable of constituting CXCL2 with the remaining portion, and removing any protecting group the resultant product may have.

Here, the condensation and the protecting group removal are conducted in accordance with methods known per se, for example, the methods indicated in (1) and (2) below:

(1) M. Bodanszky and M. A. Ondetti: *Peptide Synthesis*, Interscience Publishers, New York (1966)
(2) Schroeder and Luebke: *The Peptide*, Academic Press, New York (1965).

CXCL2 thus obtained can be purified or isolated by a known method of purification. Here, as examples of the method of purification, solvent extraction, distillation, column chromatography, liquid chromatography, recrystallization, combinations thereof and the like can be mentioned.

When the thus-obtained CXCL2 is in a free form, the free form can be converted into a suitable salt form by a known method or an analogue thereto, and on the other hand, when the CXCL2 is obtained in the form of a salt, it can be converted into the free form or in the form of a different salt by a known method or an analogue thereto.

Furthermore, CXCL2 can also be produced by culturing a transformant comprising a nucleic acid encoding the same, and separating and purifying CXCL2 from the obtained culture. The nucleic acid encoding CXCL2 may be DNA or RNA, or DNA/RNA chimera, preferably DNA. Additionally, the nucleic acid may be double-stranded or single-stranded. In the case of a double-stranded nucleic acid, it may be a double-stranded DNA, a double-stranded RNA, or a DNA:RNA hybrid. In the case of a single strand, it may be a sense strand (that is, coding strand), or an antisense strand (that is, non-coding strand).

Examples of the DNA encoding CXCL2 include genome DNA, cDNA derived from human cells, synthetic DNA and the like. Genome DNA encoding CXCL2 can be directly amplified by Polymerase Chain Reaction (hereinafter to be abbreviated as "PCR method") by using, as a template, a genome DNA fraction prepared from any cell of the aforementioned animals [for example, hepatocyte, splenocyte, nerve cell, glial cell, pancreatic β cell, myelocyte, mesangial cell, Langerhans' cell, epidermal cell, epithelial cell, goblet cell, endothelial cell, smooth muscle cell, fibroblast, fibrocyte, myocyte, adipocyte, immunocyte (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte or interstitial cell, or corresponding progenitor cell, stem cell or cancer cell thereof, and the like] of said animal or any tissue where such cells are present [for example, brain or any portion of the brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, lung, gastrointestinal tract (e.g., large intestine, small intestine), blood vessel, heart, thymus, spleen, submandibular gland, peripheral blood, prostate, testicle, ovary, placenta, uterus, bone, joint, adipose tissue (e.g., brown adipose tissue, white adipose tissue), skeletal muscle and the like], and cDNA encoding CXCL2 can also be directly amplified by PCR method and Reverse Transcriptase-PCR (hereinafter to be abbreviated as "RT-PCR method") by using, as a template, a total RNA or mRNA fraction prepared from cells. Alternatively, the genome DNA and cDNA encoding CXCL2 can also be cloned by colony or plaque hybridization method or PCR method and the like from a genome DNA library and cDNA library prepared by inserting the above-mentioned genome DNA and total RNA or a fragment of mRNA into a suitable vector. The vector used for the library may be any of a bacteriophage, a plasmid, a cosmid, a phagemid and the like.

Examples of the DNA encoding CXCL2 include a DNA comprising the same or substantially the same base sequence as the base sequence shown by SEQ ID NO: 1 and the like.

As the DNA comprising the same or substantially the same base sequence as the base sequence shown by SEQ ID NO: 1, a DNA comprising a base sequence having a homology of not less than about 60%, preferably not less than about 70%, more preferably not less than about 80%, particularly preferably not less than about 90%, with the base sequence shown by SEQ ID NO: 1, and encoding a protein having an activity substantially of the same quality as the aforementioned CXCL2 and the like are used.

Base sequence homology in the present description can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3). As preferable examples of other algorithms for determining base sequence homology, the above-described amino acid sequence homology calculation algorithm can also be mentioned.

The DNA encoding CXCL2 is preferably a DNA comprising a base sequence encoding human CXCL2 protein shown by the base sequence shown by SEQ ID NO: 1.

A DNA encoding CXCL2 can be cloned by amplifying a synthesized DNA primer having a part of a base sequence encoding the CXCL2 by PCR method, or hybridizing a DNA incorporated into a suitable expression vector with a labeled DNA fragment or synthetic DNA encoding a part or whole region of CXCL2. Hybridization can be conducted according to a method known per se or a method based thereon, for example, a method described in Molecular Cloning, 2nd edition (J. Sambrook et al., Cold Spring Harbor Lab. Press, 1989) and the like. When a commercially available library is used, hybridization can be conducted according to the method described in the instruction manual attached thereto. Hybridization can preferably be conducted under highly stringent conditions.

As examples of the highly stringent conditions, conditions of a hybridization reaction in 6×SSC (sodium chloride/sodium citrate) at 45° C. followed by washing in 0.2×SSC/0.1% SDS at 65° C. once or more and the like can be mentioned. Those skilled in the art are able to easily obtain desired stringency by changing the salt concentration of the hybridization solution, hybridization reaction temperature, probe concentration, probe length, the number of mismatches, hybridization reaction time, the salt concentration of the washing solution, washing temperature and the like as appropriate. When a commercially available library is used, hybridization can be conducted according to the method described in the instruction manual attached to the library.

An expression vector comprising DNA that encodes CXCL2 can be produced by, for example, cutting out a desired DNA fragment from the DNA that encodes CXCL2, and joining the DNA fragment downstream of a promoter in an appropriate expression vector.

As the expression vector, plasmid derived from *Escherichia coli* (e.g., pBR322, pBR325, pUC12, pUC13); animal cell expression plasmid (e.g., pCY4B, pA1-11, pXT1, pRc/CMV, pRc/RSV, pcDNAI/Neo); animal virus vectors such as retrovirus, vaccinia virus, adenovirus and the like, and the like are used.

The promoter may be any promoter, as long as it is appropriate for the host used to express the gene.

For example, when the host is an animal cell, SRα promoter, SV40 promoter, LTR promoter, CMV (cytomegalovirus) promoter, RSV (Rous sarcoma virus) promoter, MoMuLV (Moloney murine leukemia virus) LTR, HSV-TK (simple herpes virus thymidine kinase) promoter and the like are used. Of these, CMV promoter, SRα promoter and the like are preferable.

When the host is a bacterium of the genus *Escherichia*, the trp promoter, the lac promoter, the recA promoter, the $\lambda P_L$ promoter, the lpp promoter, the T7 promoter and the like are preferred.

Useful expression vectors include, in addition to the above, those optionally harboring an enhancer, a splicing signal, a polyA addition signal, a selection marker, an SV40 replication origin (hereinafter also abbreviated as SV40ori) and the like. As examples of the selection marker, the dihydrofolate reductase (hereinafter also abbreviated as dhfr) gene [methotrexate (MTX) resistance], the ampicillin resistance gene (hereinafter also abbreviated as $Amp^r$), the neomycin resistance gene (hereinafter also abbreviated as $Neo^r$, G418 resistance) and the like can be mentioned. In particular, when a Chinese hamster cell lacking the dhfr gene is used in combination with the dhfr gene as the selection marker, a target gene can also be selected using a thymidine-free medium.

Where necessary, a base sequence encoding a signal sequence suitable for a host (signal codon) may be added (or substituted with native signal codon) to the 5'-terminal side of a DNA encoding CXCL2 or a partial peptide thereof. For example, when the host is the genus *Escherichia*, PhoA signal sequence, OmpA signal sequence and the like are used; when the host is an animal cell, insulin signal sequence, α-interferon signal sequence, antibody molecule signal sequence and the like are used.

CXCL2 can be produced by transforming a host with an expression vector comprising the above-mentioned DNA encoding CXCL2, and cultivating the obtained transformant.

As the host, for example, the genus *Escherichia*, animal cell and the like are used.

As the genus *Escherichia*, for example, *Escherichia coli* K12·DH1 [Proc. Natl. Acad. Sci. USA), vol. 60, 160(1968)], *Escherichia coli* JM103 [Nucleic Acids Research, vol. 9, 309(1981)], *Escherichia coli* JA221 [Journal of Molecular Biology, vol. 120, 517(1978)], *Escherichia coli* HB101 [Journal of Molecular Biology, vol. 41, 459(1969)], *Escherichia coli* C600 [Genetics, vol. 39, 440(1954)] and the like are used.

As the animal cell, for example, monkey COS-7 cell, monkey Vero cell, Chinese hamster ovary cell (hereinafter to be abbreviated as CHO cell), dhfr gene-deficient CHO cell (hereinafter to be abbreviated as CHO(dhfr$^-$) cell), mouse L cell, mouse AtT-20 cell, mouse myeloma cell, ratGH3 cell, human FL cell and the like are used.

Transformation can be carried out according to the kind of host in accordance with a publicly known method.

The genus *Escherichia* can be transformed, for example, in accordance with the methods described in Proc. Natl. Acad. Sci. USA, vol. 69, 2110 (1972), Gene, vol. 17, 107 (1982) and the like.

An animal cell can be transformed, for example, in accordance with a method described in Saibo Kogaku (Cell Engineering), extra issue 8, Shin Saibo Kogaku Jikken Protocol (New Cell Engineering Experimental Protocol), 263-267 (1995), published by Shujunsha, or Virology, Vol. 52, 456 (1973).

Cultivation of a transformant can be carried out according to the kind of host in accordance with a publicly known method.

As an example of the medium used for culturing a transformant whose host is a bacterium of the genus *Escherichia*, a M9 medium supplemented with glucose and a casamino acid [Miller, Journal of Experiments in Molecular Genetics, 431-433, Cold Spring Harbor Laboratory, New York 1972] is preferable. As required, in order to increase promoter efficiency, a chemical agent such as 3β-indolylacrylic acid may be added to the medium.

Cultivation of a transformant whose host is a bacterium of the genus *Escherichia* is normally carried out at about 15° C. to about 43° C. for about 3 to about 24 hours. Where necessary, the culture may be aerated or agitated.

Useful medium for cultivating a transformant whose host is an animal cell include, for example, minimum essential medium (MEM) comprising about 5-about 20% fetal bovine serum [Science, vol. 122, 501 (1952)], Dulbecco's modified Eagle medium (DMEM) [Virology, vol. 8, 396(1959)], RPMI1640 medium [The Journal of the American Medical Association, vol. 199, 519(1967)], 199 medium [Proceeding of the Society for the Biological Medicine, vol. 73, 1(1950)] and the like. The medium's pH is preferably about 6 to about 8. Cultivation is normally carried out at about 30° C. to about 40° C. for about 15 to about 60 hours. As necessary, the culture may be aerated or agitated.

As described above, CXCL2 can be produced in a cell of the transformant or outside the cell.

CXCL2 can be separated and purified from the culture obtained by cultivating the aforementioned transformant according to a method known per se.

For example, when CXCL2 is extracted from a cultured bacterium or cytoplasm of cell, a method is used as appropriate wherein bacteria or cells are collected from the culture by a known means, suspended in an appropriate buffer solution, and disrupted by means of sonication, lysozyme and/or freeze-thawing and the like, after which a crude extract of soluble protein is obtained by centrifugation or filtration. The buffer solution may comprise a protein denaturing agent such as urea or guanidine hydrochloride and a surfactant such as Triton X-100™. In addition, when CXCL2 is secreted outside the fungus (cell), a method of separating a culture supernatant by centrifugation, filtration or the like from a culture, and the like are used.

Isolation and purification of CXCL2 contained in the thus-obtained soluble fraction and culture supernatant can be conducted according to a method know per se. Useful methods include methods based on solubility, such as salting-out and solvent precipitation; methods based mainly on molecular weight differences, such as dialysis, ultrafiltration, gel filtration, and SDS-polyacrylamide gel electrophoresis; methods based on charge differences, such as ion exchange chromatography; methods based on specific affinity, such as affinity chromatography; methods based on hydrophobicity differences, such as reversed-phase high performance liquid chromatography; and methods based on isoelectric point differences, such as isoelectric focusing. These methods can be combined as appropriate.

The presence of the thus-obtained CXCL2 can be confirmed by enzyme immunoassay, Western blotting and the like using an antibody against CXCL2.

In the present invention, the CXCL2 expression inducing agent is not particularly limited as long as it is a compound capable of expressing CXCL2. For example, synthesized double stranded RNA (e.g., polyinosinic-polycytidylic acid (PolyI:C)), lipopolysaccharide, leukotriene 4, platelet-activating factor (PAF), angiotensin II (Ang II), tumor necrosis factor-α (TNF-α), interleukin-17 (IL-17) and the like can be mentioned.

In the present invention, the synthesized double stranded RNA is not particularly limited as long as it is a synthetic RNA that forms a double strand by hydrogen binding between base pairs and expresses CXCL2 by transferring TLR3 signal. For example, PolyI:C formed by an RNA strand consisting only of inosine as the base and an RNA strand consisting only of cytidine as the base can be mentioned. In the present invention, moreover, PolyI:C preferably has a molecular weight of about 100 kDa-about 110 kDa. In the present invention, furthermore, PolyI:C preferably has a length of about 140 bp-about 180 bp.

A pharmaceutical composition containing HVJ-E and CXCL2 obtained as mentioned above (unless particularly indicated, in the descriptions relating to pharmaceutical compositions, CXCL2 includes not only CXCL2 protein but also nucleic acid comprising a base sequence encoding CXCL2 and a CXCL2 expression inducing agent) can be provided as an anti-cancer agent.

In the Examples mentioned below in the present specification, a pharmaceutical composition containing HVJ-E and CXCL2 showed a tumor proliferation suppressive effect in tumor-bearing mice more than HVJ-E alone, CXCL2 alone or PolyI:C alone. From the above, it is suggested that a pharmaceutical composition containing HVJ-E and CXCL2 can treat the development and progression of cancer. Therefore, a pharmaceutical composition containing HVJ-E and CXCL2 can be used as an anti-cancer agent.

Examples of the subject of administration of the pharmaceutical composition of the present invention containing HVJ-E and CXCL2 include humans and other warm-blooded animals (e.g., mouse, rat, rabbit, sheep, swine, bovine, cat, dog, monkey, avian and the like).

Cancer as an application target of the pharmaceutical composition of the present invention containing HVJ-E and CXCL2 is not particularly limited as long as it is, for example, solid cancer. Examples thereof include, but are not limited to, melanoma, lung cancer, mesothelioma, tongue cancer, esophagus cancer, gastric cancer, liver cancer, large intestine cancer, prostate cancer, kidney cancer, bladder cancer, breast cancer, uterine cancer, ovarian cancer, brain tumor, thyroid cancer, angiosarcoma, osteosarcoma, chondrosarcoma, rhabdomyosarcoma, leiomyosarcoma and the like. Of these, melanoma can be preferably mentioned.

The pharmaceutical composition of the present invention comprising HVJ-E and CXCL2 is of low toxicity, and can be administered as a liquid as it is, or as an appropriate dosage form of pharmaceutical composition, to humans or other warm-blooded mammals (e.g., mouse, rat, rabbit, sheep, swine, bovine, cat, dog, monkey, avian and the like) orally or parenterally (e.g., intravascular administration, subcutaneous administration and the like), parenteral administration is preferable.

As examples of the composition for parenteral administration, injections, suppositories and the like are used; the injections may include dosage forms such as intravenous injections, subcutaneous injections, intracutaneous injections, intramuscular injections and drip infusion injections. Such an injection can be prepared according to a publicly known method. An injection can be prepared by, for example, dissolving, suspending or emulsifying the above-mentioned HVJ-E and CXCL2 of the present invention in a sterile aqueous or oily solution in common use for injections. As examples of aqueous solutions for injection, physiological saline, an isotonic solution comprising glucose or another auxiliary drug, and the like can be used, which may be used in combination with an appropriate solubilizer, for example, alcohol (e.g., ethanol), polyalcohol (e.g., propylene glycol, polyethylene glycol), non-ionic surfactant [e.g., polysorbate 80, HCO-50 (polyoxyethylene (50 mol) adduct of hydrogenated castor oil)] and the like. As examples of oily solutions, sesame oil, soybean oil and the like can be used, which may be used in combination with benzyl benzoate, benzyl alcohol and the like as solubilizers. The prepared injection solution is preferably filled in an appropriate ampoule. Suppositories used for rectal administration may be prepared by mixing the above-mentioned HVJ-E and CXCL2 with an ordinary suppository base.

As the composition for oral administration, solid or liquid dosage forms, specifically tablets (including sugar-coated tables and film-coated tablets), pills, granules, powders, capsules (including soft capsules), syrups, emulsions, suspensions and the like can be mentioned. Such a composition is produced by a publicly known method, and may comprise a carrier, diluent or excipient in common use in the field of pharmaceutical making. As examples of the carrier or excipient for tablets, lactose, starch, sucrose, magnesium stearate and the like can be used.

For administration to adult cancer patients by injection, for example, the above-mentioned pharmaceutical composition of the present invention containing HVJ-E and CXCL2 can be administered by direct injection of HVJ-E and CXCL2 to a tumor site or the vicinity thereof. The dose thereof can be appropriately determined by a doctor or medical professional in consideration of the tumor size, age, body weight and condition of the patients and the like. When the tumor volume is not more than 1,000 mm$^3$ (e.g., about 200 mm$^3$ and the like), the dose of HVJ-E per administration to one tumor site can be set to 3 HAU-6,000,000 HAU, preferably 30 HAU-3,000,000 HAU, further preferably 300 HAU-1,500,000 HAU, (e.g., 8,000 HAU-37,000 HAU). It is preferably not more than 100,000 HAU/kg body weight. As for the dose of CXCL2, when the tumor volume is not more than 1,000 mm$^3$ (e.g., about 200 mm$^3$ and the like), the dose of CXCL2 per administration to one tumor site can be set to 0.001 ng-1,000 µg, preferably 0.01 ng-500 µg, more preferably 0.1 ng-250 µg (e.g., 0.96 ng-4.4 ng). The dose of a nucleic acid containing a base sequence encoding CXCL2 may be a nucleic acid amount corresponding to the above-mentioned dose of CXCL2. When the tumor volume is not more than 1,000 mm$^3$ (e.g., about 200 mm$^3$ and the like), the dose of a nucleic acid containing a base sequence encoding CXCL2 per administration to one tumor site can be set to 0.15 µg-6 mg, preferably 1.5 µg-3 mg, more preferably 15 µg-1,500 µg (e.g., 160 µg-740 µg). As the dose of, for example, PolyI:C as a CXCL2 expression inducing agent when the tumor volume is not more than 1,000 mm$^3$ (e.g., about 200 mm$^3$ and the like), the dose of CXCL2 per administration to one tumor site can be set to 0.1 µg-4 mg, preferably 1 µg-2 mg, further preferably 10 µg-1 mg (e.g., 80 µg-741 µg). The anti-cancer effect of HVJ-E itself and the anti-cancer effect of CXCL2 can be combined to achieve an anti-cancer activity not realizable by separate use thereof. Thus, the doses of HVJ-E and CXCL2 can be each reduced as compared to single administration of each of HVJ-E and CXCL2, which is advantageous from the aspect of safety. In addition, the administration frequency can also be determined as appropriate by a doctor or medical professional in consideration of the tumor size, age, body weight and condition of the patient, and the like.

Each of the aforementioned compositions may comprise any other active ingredients that do not produce an unwanted interaction when formulated with HVJ-E and CXCL2 of the present invention.

In the below-mentioned Examples of the present invention, a pharmaceutical composition containing HVJ-E and CXCL2 showed an effect of converting neutrophils attracted into the tumor of tumor-bearing mice by CXCL2 to N1 type neutrophils by cytokines produced from dendritic cells stimulated with HVJ-E or by HVJ-E itself. The above suggests that a pharmaceutical composition containing HVJ-E and CXCL2 can induce N1 type neutrophils in the subject of administration and administration site. Therefore, a pharmaceutical composition containing HVJ-E and CXCL2 can be used as an N1 type neutrophil inducing agent. The subject of administration, dosage form, dose, administration route and the like may be similar to those of the anti-cancer agent of the present invention.

EXAMPLES

Cell Line and Mouse

B16-F10 mouse melanoma cell line was subjected to maintenance culture in a DMEM medium (Nacalai Tesque Inc.) containing a 10% FBS (BioWest, Nuaille, France) and 0.1 mg/ml penicillin-streptomycin mixed solution (Nacalai Tesque Inc.). Myd88−/−TRIF−/− double knockout mouse obtained by crossing 6-week-old female C57BL/6N mouse and Myd88−/−mouse purchased from Clea Japan with TRIF−/−mouse was maintained in an aseptic chamber at controlled room temperature and handled according to the Approval protocol and guidelines for animal experiment provisions of Osaka University (Suita, Japan).

Virus

HVJ (VR-105 parainfluenza Sendai/52 Z strain) was purchased from ATCC (Manassas, Va.) and prepared according to the method described in Cancer Res. 67, 227-236, 2007. Briefly, a seed solution of HVJ was injected into 10 day-old embryonated hen eggs and the eggs were cultured for 3 days at 37° C. in an incubator. After 3 days, allantoic fluid was collected from the hen eggs injected with HVJ. The recovered virus (living HVJ) was inactivated by UV irradiation (198 mJ/cm$^2$) to prepare HVJ-E.

Poly I:C and MLA

Artificial monophosphoryl Lipid A (MLA) was purchased from Invivogen (San Diego, USA). Poly I:C (about 100 kDa-110 kDa; about 140 bp-about 180 bp) was purchased from Sigma-Aldrich Japan (Tokyo, Japan).

MTS Assay

The survival of cell was detected using CellTiter 96 Aqueous One Solution Cell Proliferation Assay kit (Promega). Cells were treated with poly I:C, HVJ-E or CXCL2 in a dose-dependent manner, and 100 μl CellTiter 96 Aqueous One Solution was added to the medium (1 mL). Using 96-well Mithras LB 940 Multimode Microplate Reader (Berthold Technologies GmbH & Co. KG, Bad Wildbad, Germany), absorbance was measured at 490 nm.

Tumor Inoculation Test

B16-F10 mouse melanoma cells (10$^6$ cells) suspended in 50 μl PBS were intradermally injected into the dorsal of C57BL/6N mice. After 6 days when the tumor diameter became 3-5 mm, HVJ-E (particles number 2.5×10$^9$ (2,500 HAU) or particle number 5.0×10$^9$ (5,000 HAU)), HVJ-E (particles number 2.5×10$^9$ (2,500 HAU)) combined with poly I:C (25 μg or 50 μg), recombinant CXCL-2 (Biolegend) (0.3 ng), poly I:C (25 μg) or HVJ-E (particle number 2.5×10$^9$ (2,500 HAU)) combined with CXCL2 (0.3 ng), each suspended in a total amount of 50 μl of PBS, was intratumorally injected to the mice every two days 3 times in total. The tumor volume was measured using a vernier caliper under blind trial and calculated using the following formula:

$$\text{tumor volume (mm}^3\text{)}=\text{length}\times(\text{width})^2/2$$

Cytokine Array of Tumor Tissue

At 24 hr after the final injection of HVJ-E, poly I:C, CXCL2, HVJ-E+poly I:C or HVJ-E+CXCL2, tumor tissues were collected from the tumor-bearing mice. The collected tissues were immersed in PBS and homogenized for 20 sec at 2,500 rpm using Multi-Beads Shocker (Yasui Kikai Co. Osaka, Japan). After homogenizing, Triton X-100 at a final concentration of 0.1% was added together with a protease inhibitor. The obtained sample was frozen at −80° C. and thawed followed by the centrifugation for 5 min at 10,000× g, and cell debris was removed to give a tumor tissue lysate. Tumor tissue lysate containing 400 μg equivalent amount of protein and cytokine m array panel A (R&D Systems, Minneapolis, Minn.) was used for cytokine array, and assay was performed according to the manual. The results were analyzed by ImageQuant TL (GE Healthcare).

Plasmid and Gene Construct

Mouse CXCL2 gene was purchased from Sino Biological Inc. (North Wales, USA). Using iProof™ High-Fidelity DNA polymerase (Bio-Rad) and the following primers, CXCL2 gene was amplified:

```
Forward:
                                        (SEQ ID NO: 3)
5'-AAGCTTGCCACCATGGCCCCTCCCACCT-3'

Reverse:
                                        (SEQ ID NO: 4)
5'-CTCGAGTCAGTTAGCCTTGCCTTTG-3'
```

For gene therapy experiment, CXCL2 gene was cloned to pCY4B vector.

Gene Therapy Using HVJ-E-Supported CXCL2 Expression Vector

In a gene therapy experiment, HVJ-E was used to transduce CXCL2 expression vector plasmid (pCY4B-CXCL2) into B16-F10 tumor derived from C57BL6/N mouse. HVJ-E derived from hen egg was treated with GenomeONE transfection kit buffer (GenomeONE; Ishihara-Sangyo Kaisha Ltd., Osaka, Japan). Along with pCY4B-CXCL2 (50 μg/50 μl per mouse), HVJ-E (2500 HAU) was intratumorally injected to B16-F10 bearing mouse every two days 3 times in total. The tumor size was observed up to day 25.

Preparation of Spleen Cells

The spleen was removed from C57BL/6N mouse. The cells derived from the spleen were passed through a 40-μm mesh and hemolyzed with a hemolysis buffer (Immuno-Biological Laboratories Co., Ltd.). The bone marrow was washed out from tibia and femur with the medium. The cells derived from the bone marrow were passed through a 40-μm mesh to isolate mouse dendritic cells. After washing, the cells were cultured in a medium containing 10 ng/mL recombinant mouse GM-CSF. After 6 days, CD11c expression was evaluated by flow cytometry to identify nonadhesive or loosely adhered cells as dendritic cells.

ELISpot Assay

PBS, poly I:C, CXCL2, HVJ-E, HVJ-E+poly I:C or HVJ-E+CXCL2 was intratumorally injected to B16-F10 bearing C57BL6/N mice every 2 days 3 times in total. At 10 days after the final injection, the spleen was removed from the mouse, and spleen cells were prepared from the spleen as described in the above-mentioned preparation protocol of spleen cells. B16-F10 melanoma cells were treated with mitomycin C (15 μg/ml) for 45 min. The spleen cells and the B16-F10 melanoma cells treated with mitomycin C were mixed at a ratio of 10:1. After 48 hr, non-adhesive spleen cells were collected, and ELISpot assay was conducted using Mouse IFN-γ Development Module (R&D Systems) and ELISpot Blue Color Module (R&D Systems). Thereafter, IFN-γ secreting cells were counted.

CXCL2 Neutralization and Inhibition of Neutrophil

In a CXCL1/CXCL2 neutralization experiment, a CXCL1 or CXCL2 neutralizing antibody (R&D Systems) was intraperitoneally injected in advance to B16-F10 bearing C57BL6/N mice 24 hr before intratumoral injection of PBS, HVJ-E, poly I:C or HVJ-E+poly I:C. After the final injection of PBS, HVJ-E, poly I:C or HVJ-E+poly I:C, the tumor size was observed every 2-3 days. The tumor was excised at completion of the experiment and the weight was measured.

To deplete neutrophil, before or between intratumoral injections of PBS, poly I:C, CXCL2, HVJ-E, HVJ-E+poly I:C or HVJ-E+CXCL2, a Ly-6G (1A8) antibody was intratumorally (50 μg) or intraperitoneally (100 μg) injected. After the final injection of PBS, poly I:C, CXCL2, HVJ-E, HVJ-E+poly I:C or HVJ-E+CXCL2, the tumor size was observed every 2-3 days. The tumor was excised at completion of the experiment and the weight was measured.

Quantitative Real-Time RT-PCR

Using Isogen (Wako, Osaka, Japan), total RNA was extracted from the tumor excised and washed with PBS. RNA was quantified, and 2 μg thereof was reverse transcribed into cDNA (Applied Biosystems). Using SYBR qPCR Mix (Toyobo CO., LTD) together with a primer set of mouse Ly-6G, CXCL1, CXCL2 and β-actin (below), quantitative PCR was performed. Using CFX384 Real-time system (Bio-Rad, CA, USA), the copy number of the target gene was measured. All operations were performed according to the manual.

Ly-6G

```
Forward:
                                            (SEQ ID NO: 5)
5'-TGGACTCTCACAGAAGCAAAG-3'

Reverse:
                                            (SEQ ID NO: 6)
5'-GCAGAGGTCTTCCTTCCAACA-3'

CXCL1
Forward:
                                            (SEQ ID NO: 7)
5'-GACTCCAGCCACACTCCAAC-3'

Reverse:
                                            (SEQ ID NO: 8)
5'-TGACAGCGCAGCTCATTG-3'

CXCL2
Forward:
                                            (SEQ ID NO: 9)
5'-AAAATCATCCAAAAGATACTGAACAA-3'

Reverse:
                                           (SEQ ID NO: 10)
5'-CTTTGGTTCTTCCGTTGAGG-3'

β-actin
Forward:
                                           (SEQ ID NO: 11)
5'-GGAGGGGGTTGAGGTGTT-3'

Reverse:
                                           (SEQ ID NO: 12)
5'-GTGTGCACTTTTATTGGTCTCAAG-3'

ICAM-1
Forward:
                                           (SEQ ID NO: 13)
5'-GTGGCGGGAAAGTTCCTG-3'

Reverse:
                                           (SEQ ID NO: 14)
5'-CGTCTTGCAGGTCATCTTAGGAG-3'

MMP8
Forward:
                                           (SEQ ID NO: 15)
5'-AACGGGAAGACATACTTCTTCATAA-3'

Reverse:
                                           (SEQ ID NO: 16)
5'-GGGTCCATGGATCTTCTTTG-3'

IFN-β
Forward:
                                           (SEQ ID NO: 17)
5'-CACAGCCCTCTCCATCAACTA-3'

Reverse:
                                           (SEQ ID NO: 18)
5'-CATTTCCGAATGTTCGTCCT-3'

TGF-β
Forward:
                                           (SEQ ID NO: 19)
5'-TGGAGCAACATGTGGAACTC-3'

Reverse:
                                           (SEQ ID NO: 20)
5'-GTCAGCAGCCGGTTACCA-3'
```

Flow Cytometry Analysis of Tumor

Tumor was excised from a mouse and shredded in a digestion buffer containing 2% FBS and 2.5 mg/mL collagenase A (Roche, Indianapolis, Ind.). The shredded material was incubated in a digestion buffer at 37° C. for 1 hr with shaking, filtered through a 70-μm filter and washed twice with PBS. The collected cells were stained with the following fluorescence labeled antibody: CD45 (30-F11), CD11b (M1/70), Ly-6G (1A8), ICAM-1 (YN1/1.74) (BioLegend Inc.) and Fas (eBioscience, San Diego, USA). All flow cytometry was performed on CSCanto™ II (Becton, Dickinson and Company, USA) and analyzed using FlowJo software (FLOWJO LLC, Oregon, USA).

Treatment of Neutrophil with HVJ-E

Using Neutrophil Isolation Kit (Miltenyi Biotec, Bergisch Gladbach, Germany), neutrophil was isolated from the mouse bone marrow by MACS with an anti-neutrophil antibody according to the manual. $2 \times 10^5$ neutrophils in a 96 well plate were treated with 500 m.o.i. of HVJ-E for 24 hr. As a different method, mouse dendritic cells ($2 \times 10^5$) derived from the bone marrow isolated as mentioned above were treated with 500 m.o.i. of HVJ-E for 24 hr. The cell suspension was centrifuged at 18,500×g for 5 min to prepare the conditioned medium free of dendritic cells and HVJ-E. The neutrophil ($2 \times 10^5$) was cultured for 36 hr in the conditioned medium. Neutrophils cocultured with HVJ-E and neutrophils cultured in the conditioned medium were subjected to FACS, and the expression of Fas and ICAM-1 was analyzed.

Statistical Analysis

Using Student's unpaired t-test by GraphPad, statistical analysis was conducted and $P<0.05$ was taken as showing a statistically significant difference.

Example 1 Antitumor Effect of Concomitant Drug of HVJ-E and PolyI:C—1

Mouse melanoma cell line B16-F10 was seeded, treated with PBS, poly I:C (0.1 μg/ml, 0.25 μg/ml or 1 μg/ml (culture for 24 hr), or 0.625 μg/ml, 1.25 μg/ml or 5 μg/ml (culture for 48 hr)), HVJ-E (1,000 moi, 2,500 moi or 10,000 moi) or HVJ-E+poly I:C (H+P) (1,000 moi+0.625 μg/ml, 2,500 moi+1.25 μg/ml or 10,000 moi+5 μg/ml), and cultured for 24 hr or 48 hr. CellTiter 96 Aqueous One Solution (100 μl) was added to the medium, and absorbance at 490 nm was measured. The results are shown in FIG. 1. In vitro, none of poly I:C, HVJ-E or HVJ-E+poly I:C (H+P) affected cell proliferation.

Figure 2:
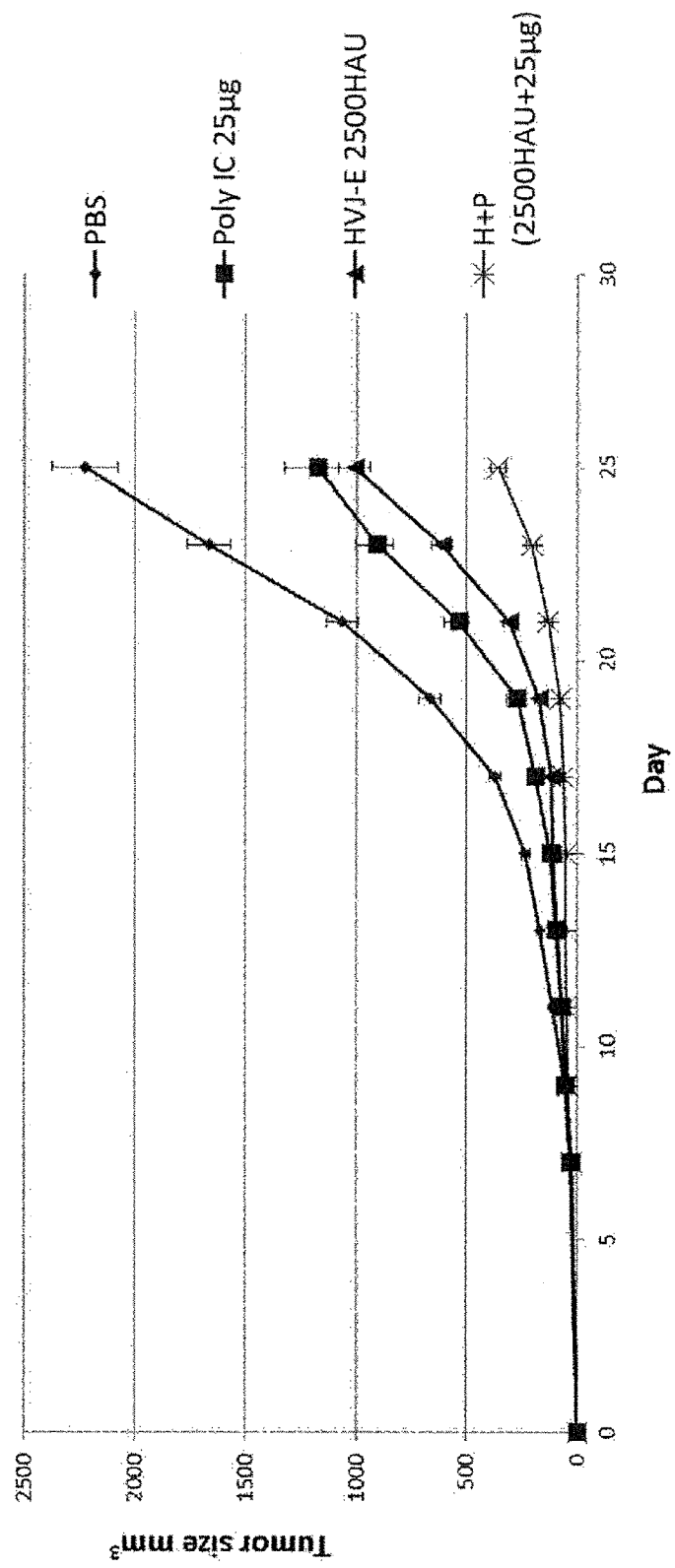
FIG. 2 shows the tumor volume when PBS, poly I:C, HVJ-E or HVJ-E+poly I:C (H+P) was administered.

In addition, PBS, poly I:C (25 μg), HVJ-E (2,500 HAU) or HVJ-E+poly I:C (H+P) (2,500 HAU+25 μg) was intratumorally injected to mouse melanoma cell line B16-F10-bearing C57BL/6N mice every two days 3 times in total, and tumor volume was measured over time. The results are shown in FIG. 2. The efficacy of HVJ-E+poly I:C (H+P) on suppressing tumor proliferation in vivo was more effective than that of poly I:C or HVJ-E.

Example 2 Antitumor Effect of Concomitant Drug of HVJ-E and PolyI:C—2

Figure 3:
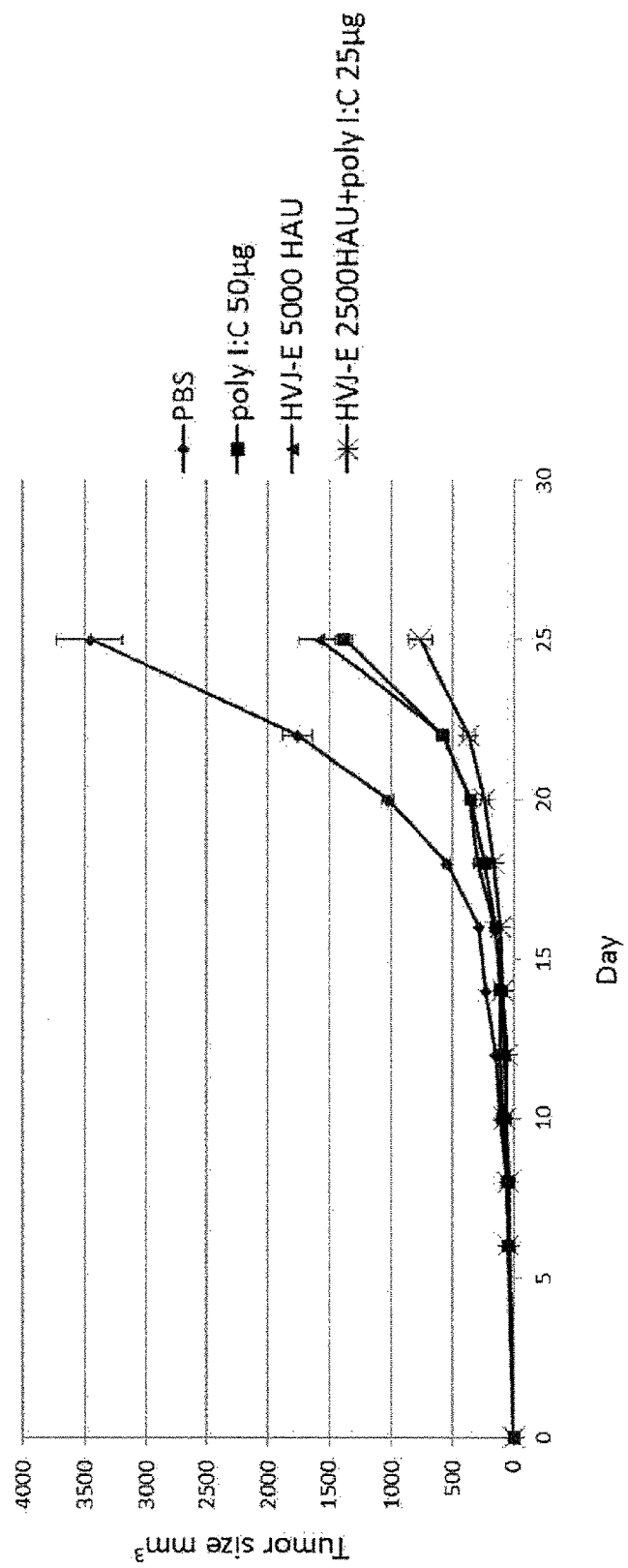
FIG. 3 shows the tumor volume when PBS, poly I:C, HVJ-E or HVJ-E+poly I:C was administered.

In Example 1, the same level of tumor proliferation suppressive effect could be confirmed in both poly I:C (25 μg) and HVJ-E (2,500 HAU). In the same manner as in Example 1, PBS, 2 times the amount of poly I:C in Example 1 (50 μg), 2 times the amount of HVJ-E in Example 1 (5,000 HAU) or HVJ-E+poly I:C (H+P) (2,500 HAU+25 μg), which is a combination of poly I:C and HVJ-E in amounts equal to Example 1, was intratumorally injected to mouse melanoma cell line B16-F10-bearing C57BL/6N mice every two days 3 times in total, and tumor volume was measured over time. The results are shown in FIG. 3. The efficacy of HVJ-E+poly I:C (H+P) (2,500 HAU+25 µg) on suppressing tumor proliferation in vivo was more effective than that of poly I:C (50 µg) or HVJ-E (5,000 HAU).

Example 3 Cytokine Induced by PolyI:C

Figure 4:
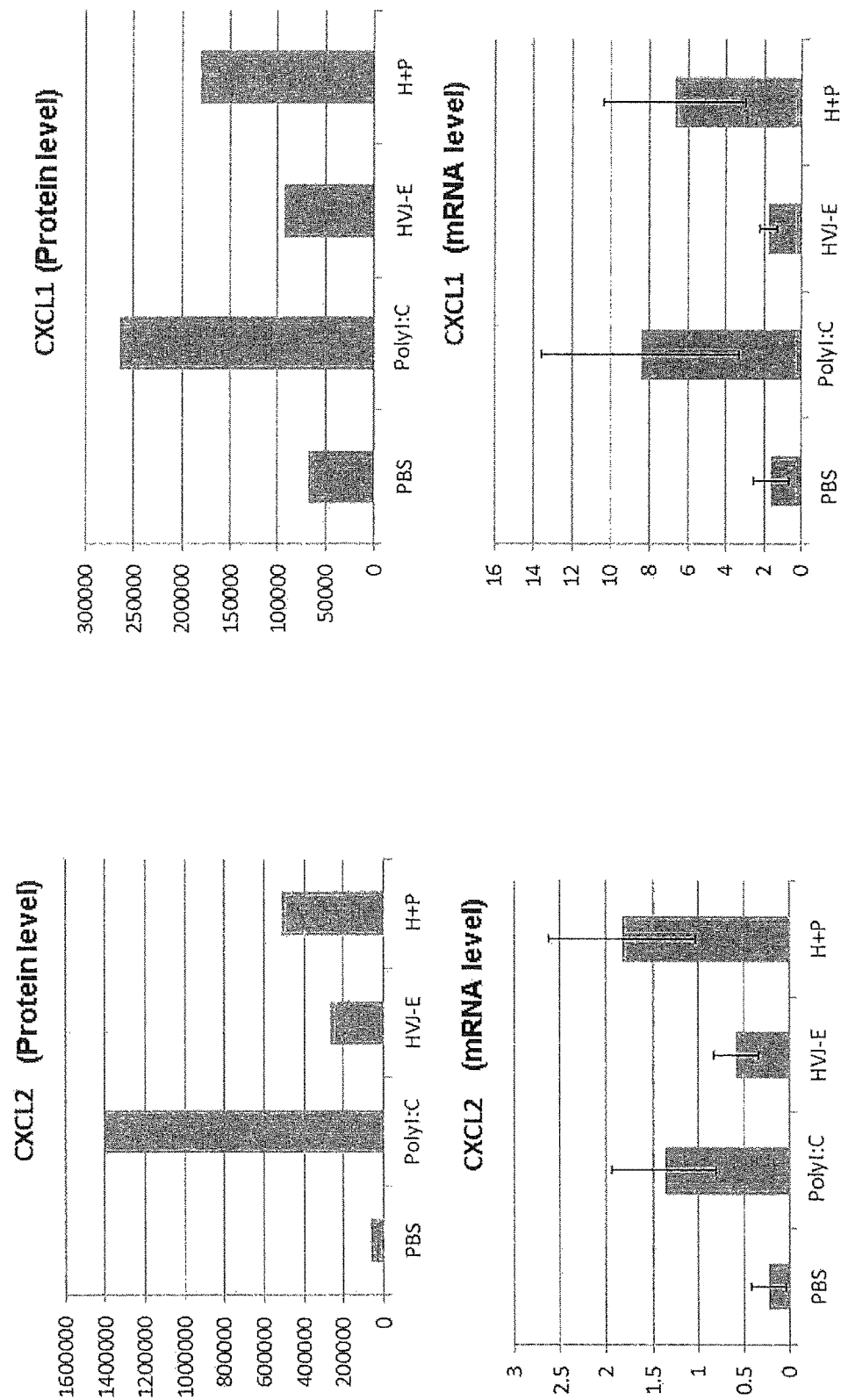
FIG. 4, the upper panel, shows comparison of the protein levels of CXCL1 and CXCL2 in tumor when PBS, poly I:C, HVJ-E or HVJ-E+poly I:C (H+P) was administered. The lower panel shows comparison of the mRNA levels of CXCL1 and CXCL2 in tumor when PBS, poly I:C, HVJ-E or HVJ-E+poly I:C (H+P) was administered.

PBS, poly I:C, HVJ-E or HVJ-E+poly I:C (H+P) was intratumorally injected to B16-F10-bearing C57BL/6N mice. Tumor tissues collected after 24 hr were homogenized in PBS. A protease inhibitor and Triton X-100 were added and the mixture was centrifuged to prepare a tumor tissue lysate. Using the tumor tissue lysate, cytokine array was performed. As a result, when PolyI:C was administered alone or in combination with HVJ-E, the protein levels of CXCL1 and CXCL2 in the tumor were increased as compared to that in tumor of the mouse without the administration of PolyI:C (FIG. 4, upper panel).

In addition, PBS, poly I:C, HVJ-E or HVJ-E+poly I:C (H+P) was intratumorally injected to B16-F10-bearing C57BL/6N mice. The tumor was excised at 24 hr of the injection, and total RNA was extracted from the tumor. Complementary DNA was obtained by reverse transcription using the prepared RNA, and quantitative PCR was performed using a primer set of mouse CXCL1, CXCL2. As a result, when PolyI:C was administered alone or in combination with HVJ-E, the mRNA levels of CXCL1 and CXCL2 in the tumor were increased as compared to that in tumor of the mouse without the administration of PolyI:C (FIG. 4, lower panel).

Figure 5:
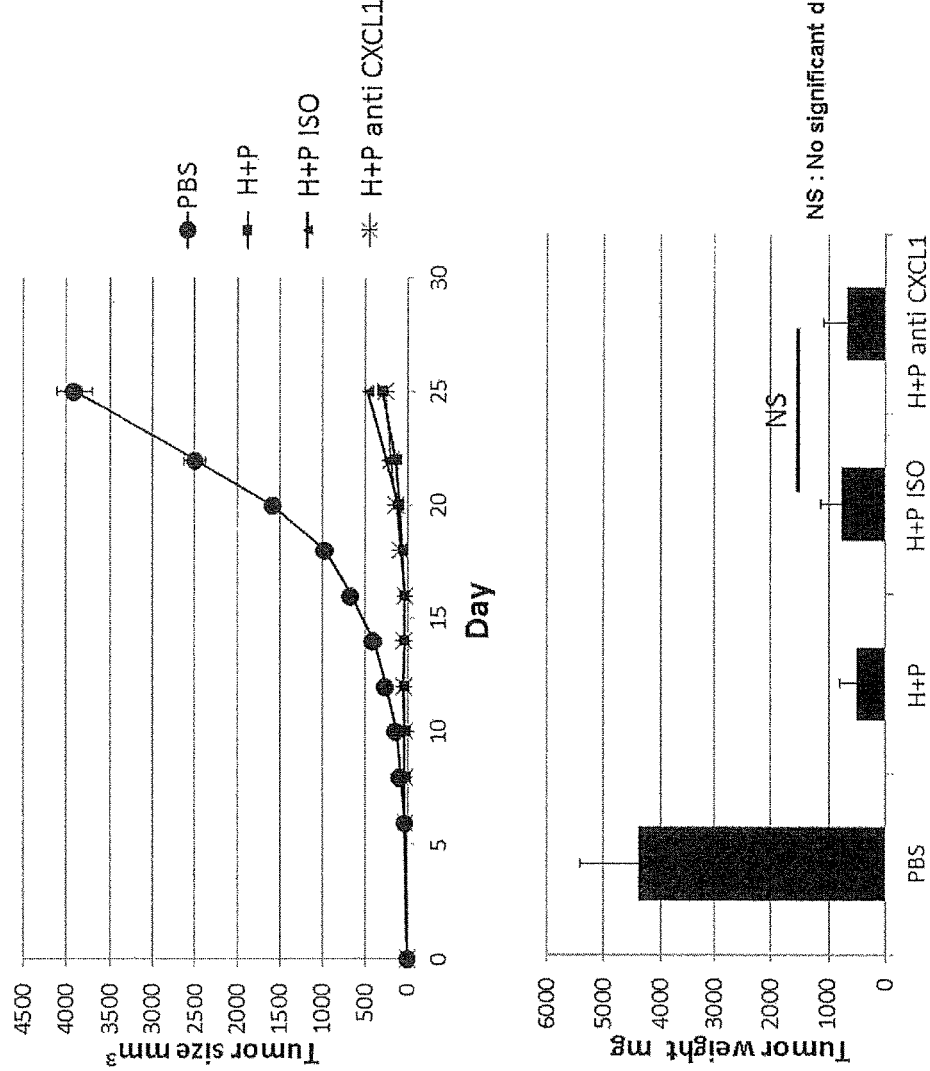
FIG. 5 shows tumor volume and tumor weight when PBS or HVJ-E+poly I:C (H+P) was administered after administration of a CXCL1 neutralizing antibody. ISO shows an antibody having no specificity to CXCL1 (Isotype Control).

Example 4 Influence of Inhibition of CXCL1 on Antitumor Effect of Concomitant Drug of HVJ-E and PolyI:C CXCL1 neutralizing antibody was intraperitoneally injected to B16-F10-bearing C57BL/6N mice, PBS or HVJ-E+poly I:C (H+P) was intratumorally injected 24 hr later, and tumor size was observed every 2-3 days. At completion of the experiment, the tumor was excised and the weight was measured. The results are shown in FIG. 5. The tumor volume and tumor weight did not change among 3 conditions; with administration of CXCL1 neutralizing antibody (H+P antiCXCL1), without administration of neutralizing antibody (H+P), and with administration of antibody having no specificity to CXCL1 (Isotype Control (ISO)) (H+P ISO). The result suggests that the tumor suppressive action of HVJ-E+poly I:C (H+P) is independent on CXCL1.

Figure 6:
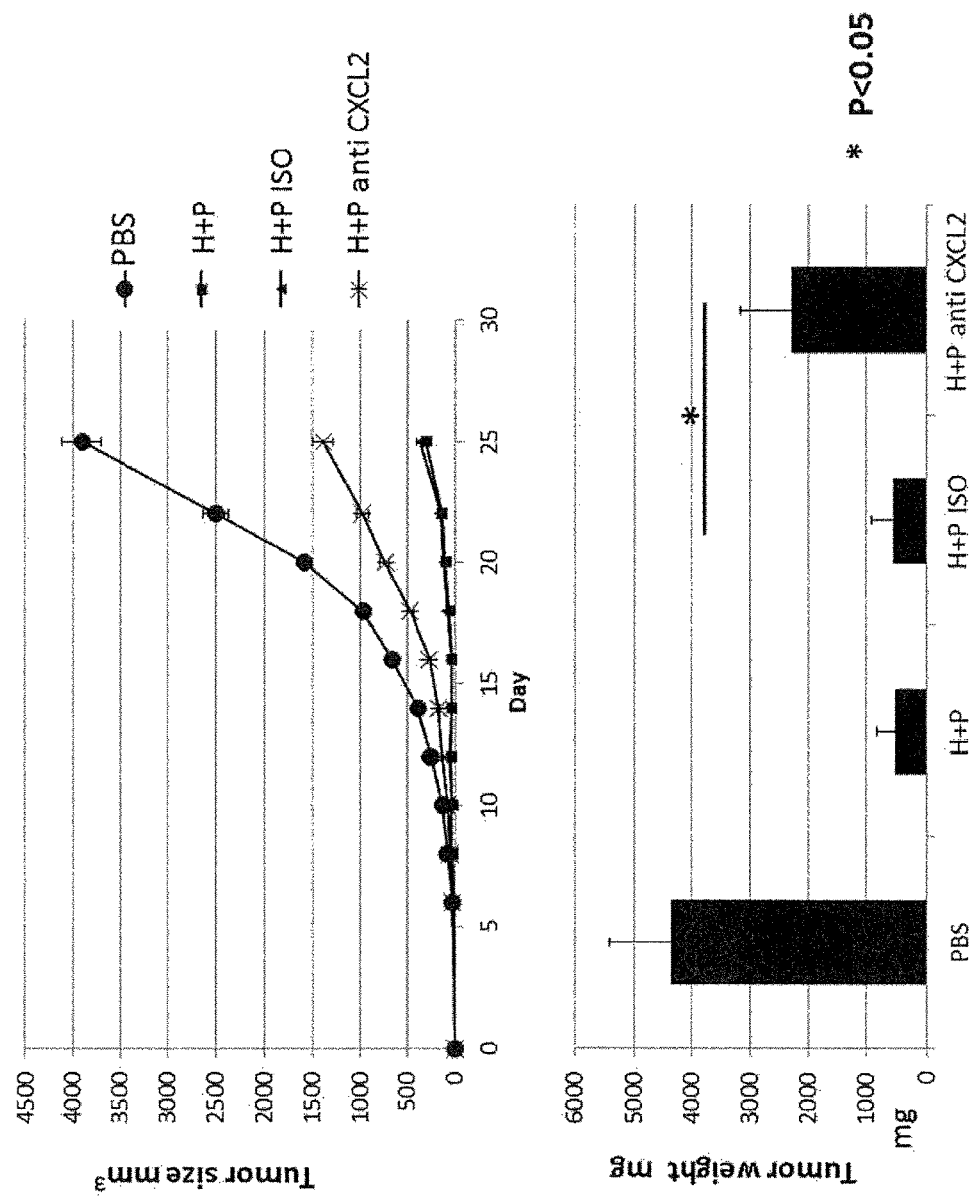
FIG. 6 shows tumor volume and tumor weight when PBS or HVJ-E+poly I:C (H+P) was administered after administration of a CXCL2 neutralizing antibody. ISO shows an antibody having no specificity to CXCL2 (Isotype Control).

Example 5 Influence of Inhibition of CXCL2 on Antitumor Effect of Concomitant Drug of HVJ-E and PolyI:C An operation was performed similar to that of Example 4 except that a CXCL2 neutralizing antibody was used instead of a CXCL1 neutralizing antibody. The tumor size and tumor weight were measured. The results are shown in FIG. 6. When a CXCL2 neutralizing antibody was administered (H+P antiCXCL2) and an antibody having no specificity to CXCL2 was administered (H+P ISO), the tumor volume changed as compared to no administration of a neutralizing antibody (H+P) (upper panel), and comparison of administration of CXCL2 neutralizing antibody (H+P antiCXCL2) and administration of an antibody having no specificity to CXCL2 (H+P ISO) revealed a significant difference in the tumor weight as well (lower panel). Therefore, it was suggested that the tumor suppressive action of HVJ-E+poly I:C (H+P) is depended on CXCL2.

Example 6 Profile of Neutrophil-Related Gene Expression in Tumor Tissue

It is known that CXCL2 has a function of chemoattractant for neutrophil. Neutrophils infiltrated into tumor are called tumor associated neutrophils (TANs), and are classified into N1 type neutrophil having a tumor proliferation suppressive activity against tumor and N2 type neutrophil having a tumor proliferation-promoting activity. A poly I:C increases CXCL2 level in tumor and a tumor suppressive action of HVJ-E+poly I:C (H+P) depends on CXCL2. Therefore, neutrophils in tumor and classification thereof were examined.

Figure 7:
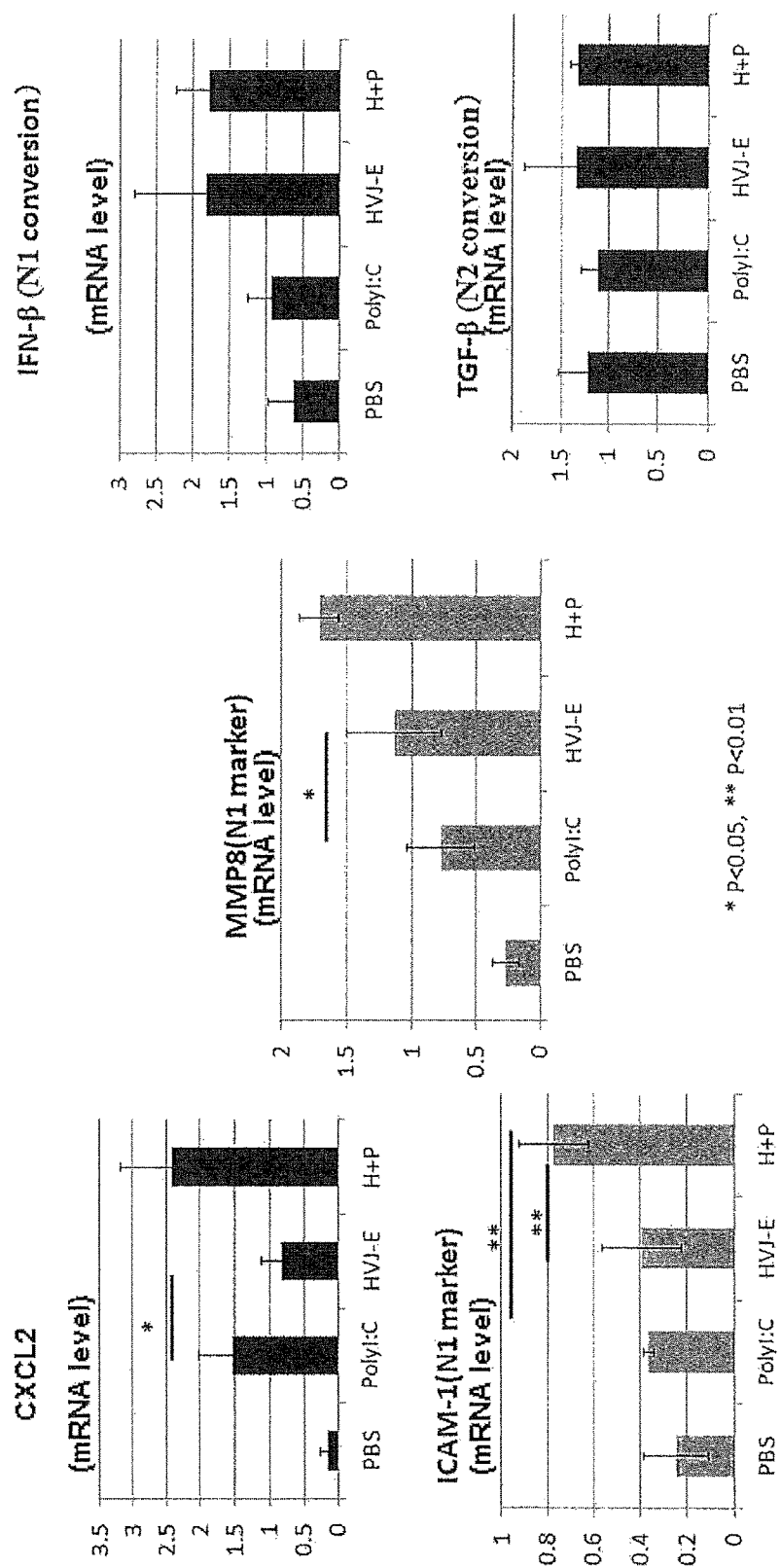
FIG. 7 shows comparison of the mRNA level of neutrophil-related gene in tumor when PBS, poly I:C, HVJ-E or HVJ-E+poly I:C (H+P) was administered.

In the same manner as in Example 3, PBS, poly I:C, HVJ-E or HVJ-E+poly I:C (H+P) was intratumorally injected to B16-F10-bearing C57BL/6N mice, the tumor was excised 24 hr later, and total RNA was extracted from the tumor. Complementary DNA was obtained by reverse transcription of the RNA, and quantitative PCR was performed using a primer set of mouse CXCL2, ICAM-1 (N1 type neutrophil marker), MMP8 (N1 type neutrophil marker), IFN-β (that converts neutrophil to N1 type neutrophil) and TGF-β (that converts neutrophil to N2 type neutrophil). The results are shown in FIG. 7. When PolyI:C was administered in single, mRNA level of CXCL2 in the tumor significantly increased as compared to that in the tumor of HVJ-E single-administered group. When HVJ-E+poly I:C (H+P) was administered, the mRNA level of N1 type neutrophil marker ICAM-1 significantly increased as compared to PolyI:C single-administered or HVJ-E single-administered group, and the mRNA level of N1 type neutrophil marker MMP8 also increased. When HVJ-E was administered in single or administered in combination with PolyI:C, the mRNA level of IFN-β which converts TANs in the tumor to N1 type increased as compared to that in the tumor of no administration of HVJ-E group, while the mRNA level of TGF-β which converts TANs in the tumor to N2 type did not change between groups.

Figure 8:
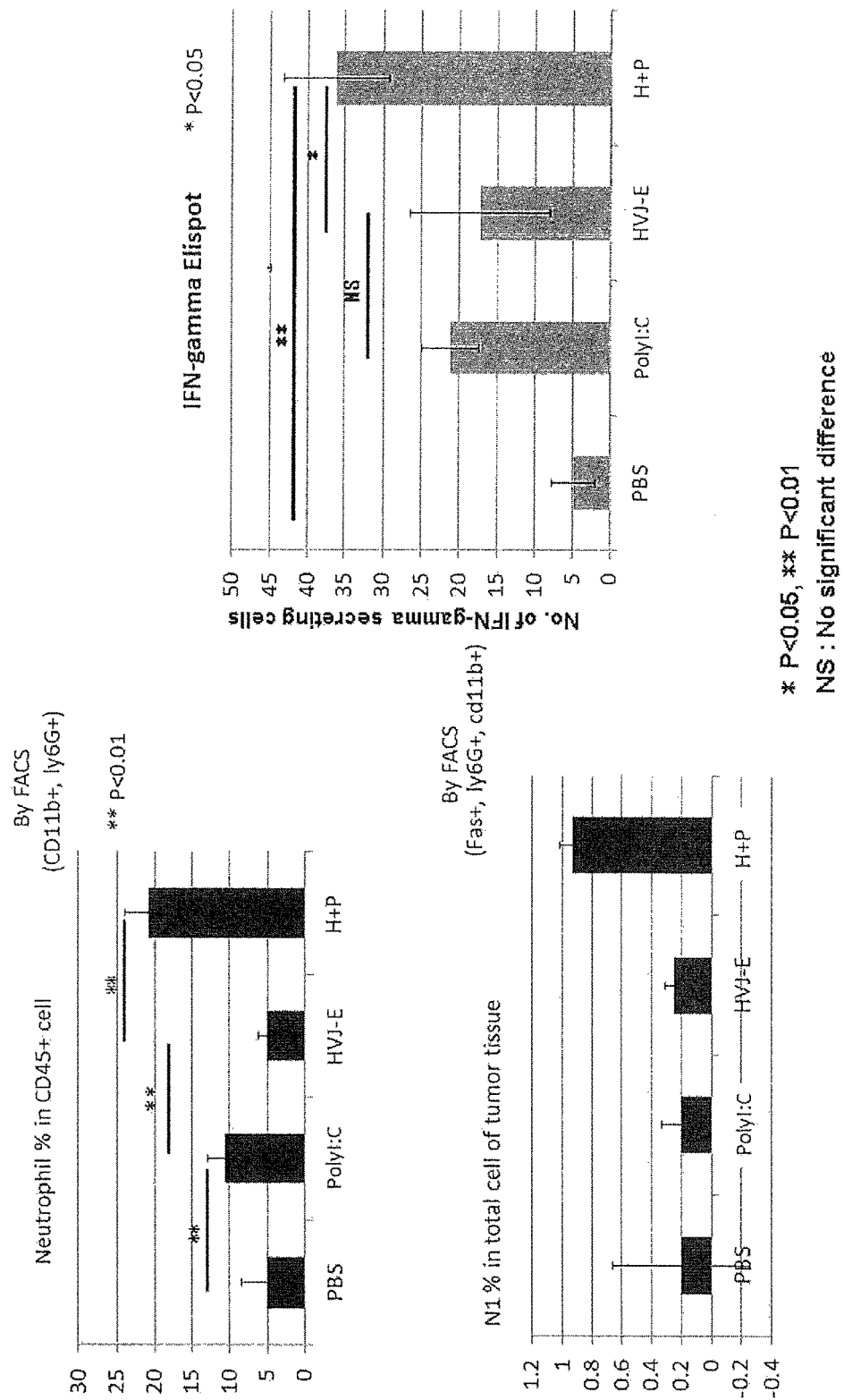
FIG. 8, upper left, shows comparison of the ratio of neutrophil in CD45+ cell population in tumor when PBS, poly I:C, HVJ-E or HVJ-E+poly I:C (H+P) was administered. Lower left shows comparison of the ratio of N1 type neutrophil in whole neutrophil in tumor when PBS, poly I:C, HVJ-E or HVJ-E+poly I:C (H+P) was administered. Right shows comparison of the number of IFN-γ secreting cells in spleen when PBS, poly I:C, HVJ-E or HVJ-E+poly I:C (H+P) was administered.

Example 7 Ratios of Neutrophil and N1 Type Neutrophil in Tumor Tissue, and IFN-γ Secreting Cell in Spleen PBS, poly I:C, HVJ-E or HVJ-E+poly I:C (H+P) was intratumorally injected to B16-F10-bearing C57BL/6N mice, the tumor excised from the mouse was treated with a digestion buffer, and the collected cells were stained with the following fluorescence labeled antibodies: CD45(30-F11), CD11b(M1/70), Ly-6G(1A8), ICAM-1(YN1/1.74) (BioLegend Inc.) and Fas (eBioscience, San Diego, USA). The stained cells were analyzed by flow cytometry. As a result, when PolyI:C was administered, the ratio of intratumoral neutrophil significantly increased as compared to that observed in the tumor of no administration of PolyI:C group (FIG. 8, upper left). When HVJ-E+poly I:C (H+P) was administered, the ratio of intratumoral N1 type neutrophil increased as compared to those observed in other groups (FIG. 8, lower left).

In addition, PBS, poly I:C, HVJ-E or HVJ-E+poly I:C (H+P) was intratumorally injected to B16-F10-bearing mice and the spleen was excised from the mouse 10 days later. Spleen cells were prepared from the spleen, mixed with B16-F10 melanoma cells treated with mitomycin C, and non-adhesive spleen cells were collected 48 hr later.

ELISpot assay was performed and IFN-γ secreting cells were counted. As a result, the number of IFN-γ secreting cells in the spleen of HVJ-E+poly I:C group (H+P) significantly increased compared to those of vehicle (PBS)-administered or HVJ-E-administered groups (FIG. 8, right).

Figure 9:
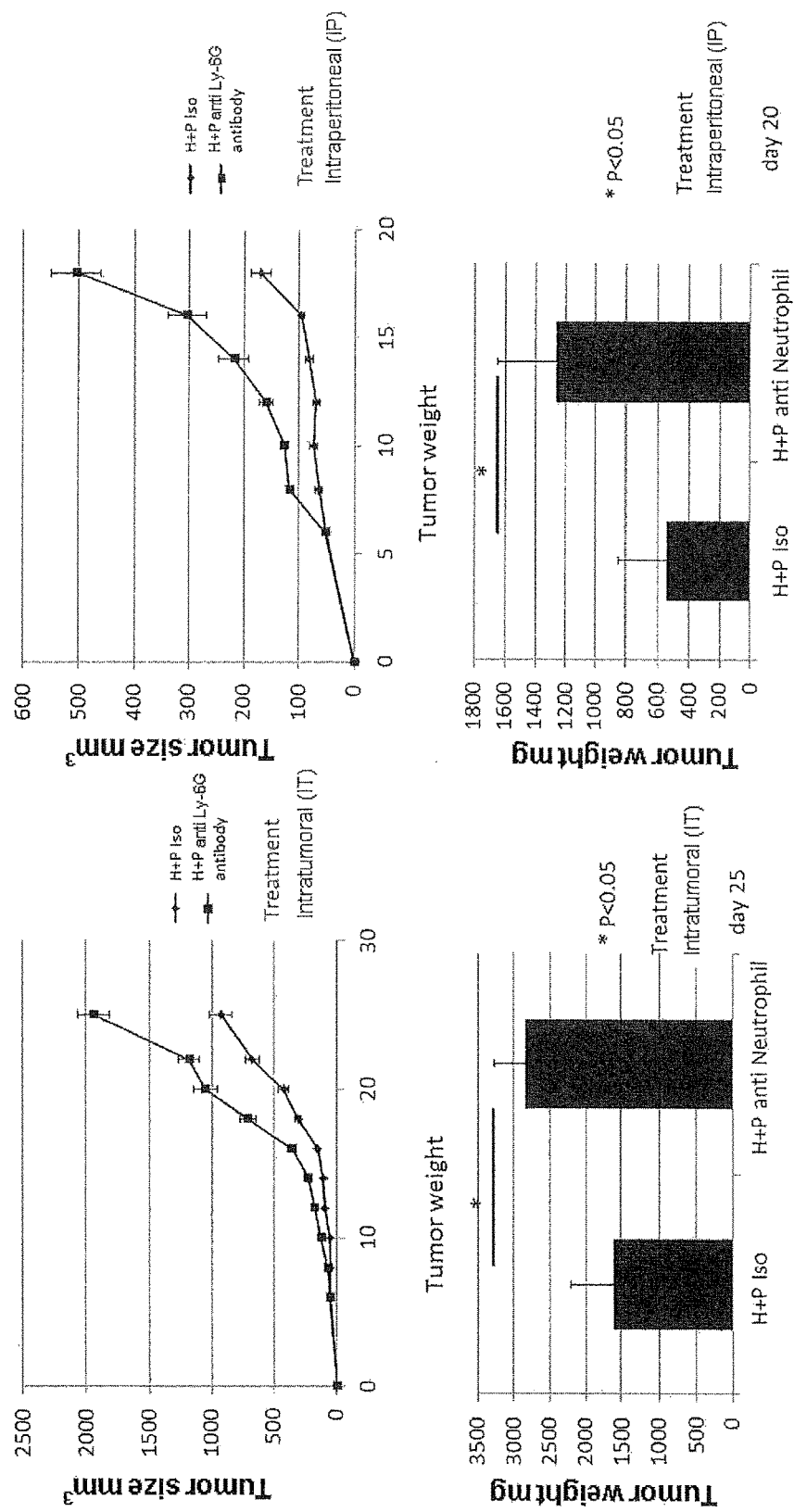
FIG. 9 shows tumor volume and tumor weight when HVJ-E+poly I:C (H+P) was administered after intratumoral or intraperitoneal administration of an anti-neutrophil antibody (anti-Ly-6G antibody or anti-Neutrophil). ISO shows an antibody having no specificity to neutrophil (Isotype Control).

Example 8 Influence of Inhibition of Neutrophil on Antitumor Effect of Concomitant Drug of HVJ-E and PolyI:C An anti-neutrophil antibody Ly-6G (1A8) was intratumorally or intraperitoneally injected to B16-F10-bearing C57BL/6N mice, HVJ-E+poly I:C (H+P) was intratumorally injected 24 hr later, and tumor size was observed every 2-3 days. At completion of the experiment, the tumor was excised and the weight was measured. The results are shown in FIG. 9. When the anti-neutrophil antibody was administered, the tumor volume increased as compared to that of the mouse without administration of the antibody, and the tumor weight also showed a significant difference. Therefore, it was suggested that the tumor suppressive action of HVJ-E+ poly I:C (H+P) depends on neutrophil.

Example 9 Antitumor Effect of Concomitant Drug of HVJ-E and CXCL2

Figure 10:
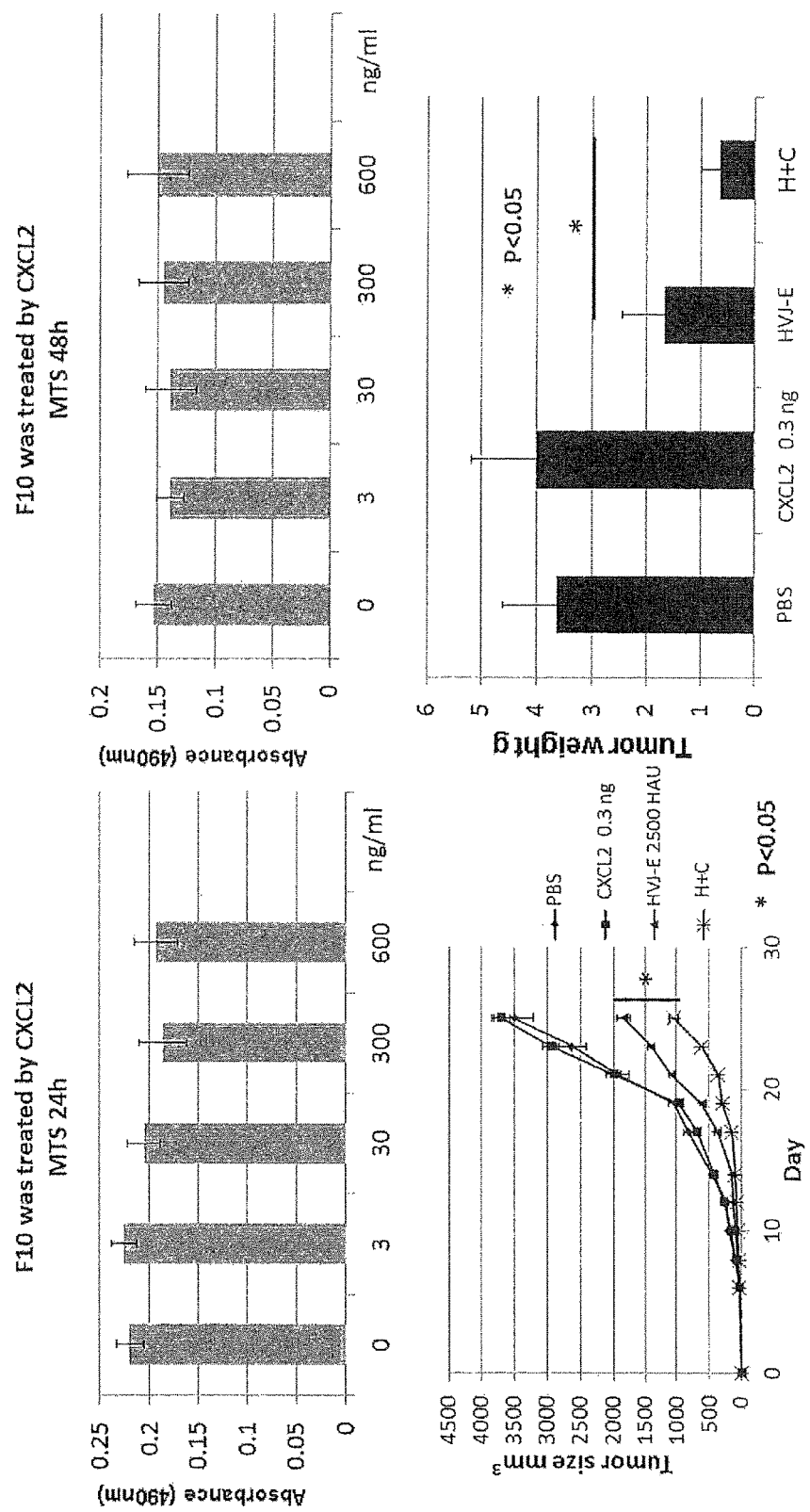
FIG. 10, upper panel, shows the results of MTS assay when CXCL2 was used. The lower panel shows tumor volume and tumor weight when PBS, CXCL2, HVJ-E or HVJ-E+CXCL2 (H+C) was administered FIG. 11, left, shows comparison of the number of IFN-γ secreting cells in spleen when PBS, CXCL2, HVJ-E or HVJ-E+CXCL2 (H+C) was administered. Right shows comparison of the number of IFN-γ secreting cells in spleen when HVJ-E (upper right) or HVJ-E+CXCL2 (H+C) (lower right) was administered after administration of an anti-neutrophil antibody (Neutrophil depletion). ISO shows an antibody having no specificity to neutrophil (Isotype Control).

Mouse melanoma cell line B16-F10 was seeded, treated with CXCL2 (0 ng/ml, 3 ng/ml, 30 ng/ml, 300 ng/ml or 600 ng/ml), and cultured for 24 hr or 48 hr. CellTiter 96 Aqueous One Solution (100 μl) was added to the medium, and absorbance at 490 nm was measured. The results are shown in FIG. 10, upper panel. In vitro, a significant difference could not be confirmed in the cell proliferation irrespective of the concentration of CXCL2.

In addition, PBS, CXCL2 (0.3 ng), HVJ-E (2,500 HAU) or HVJ-E+CXCL2 (H+C) (2,500 HAU+0.3 ng) was intratumorally injected to mouse melanoma cell line 316-F10-bearing C57BL/6N mice every two days 3 times in total, and tumor volume was measured over time. The results are shown in FIG. 10, lower panel. In vivo, CXCL2 single administration did not show a tumor suppressive effect. As compared to HVJ-E single administration, HVJ-E+CXCL2 (H+C) administration showed a higher effect on the suppression of tumor proliferation.

Figure 11:
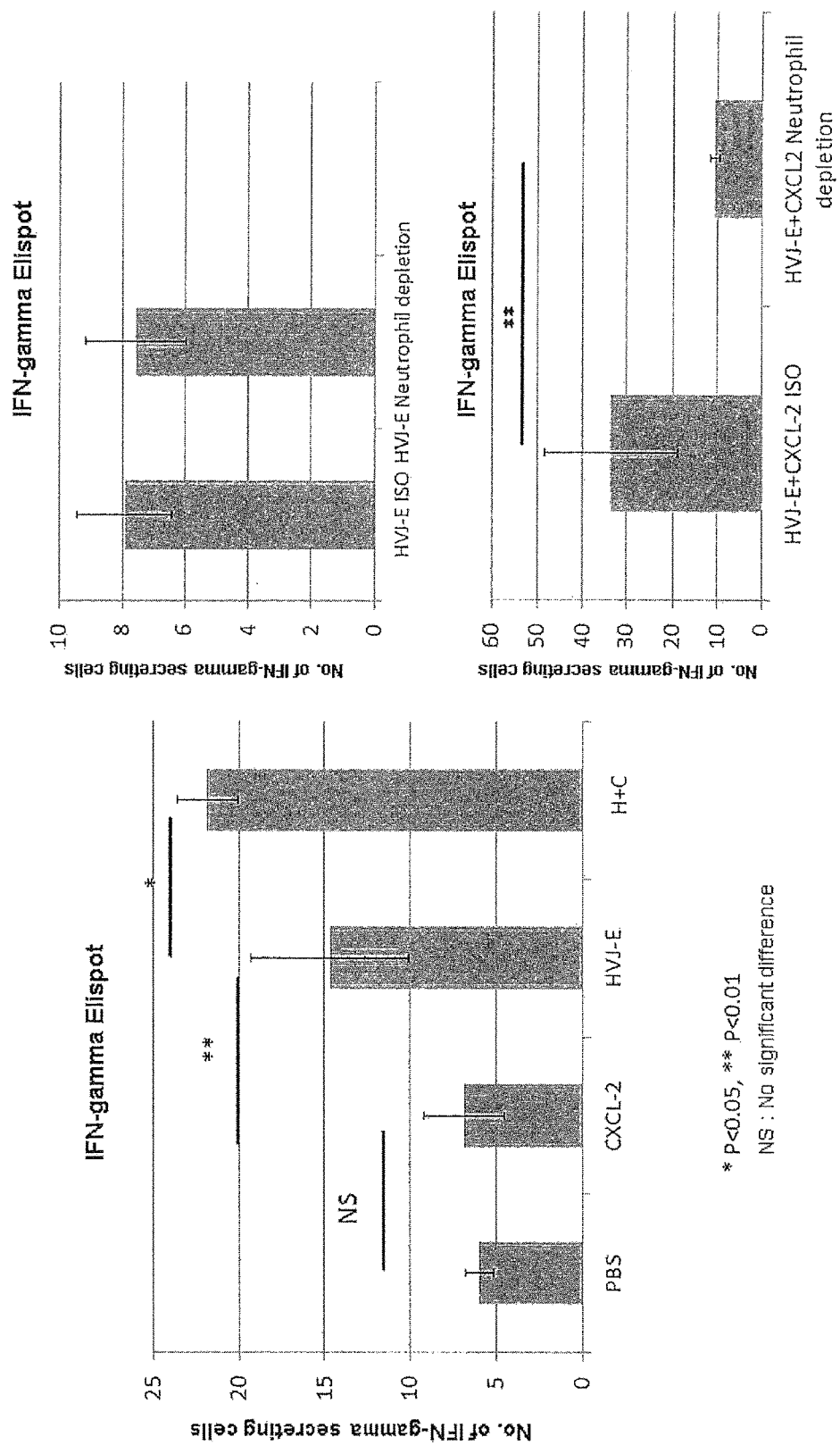

Example 10 IFN-γ Secreting Cell in Spleen and Influence of Neutrophil Inhibition An operation similar to that of Example 7 was performed except that CXCL2 was used instead of poly I:C, and IFN-γ secreting cells in the spleen were counted. As a result, the number of IFN-γ secreting cells significantly increased in the spleen of HVJ-E+CXCL2 (H+C)-administered mice, as compared to that observed in the spleen of HVJ-E single-administered mice (FIG. 11, left).

In addition, anti-neutrophil antibody Ly-6G (1A8) antibody was intraperitoneally injected to B16-F10-bearing C57BL/6N mice. An operation similar to the above was performed. ELISpot assay was performed and IFN-γ secreting cells were counted. As a result, the number of IFN-γ secreting cells did not change by neutrophil depletion when HVJ-E was administered in single (FIG. 11, upper right). On the other hand, when HVJ-E+CXCL2 (H+C) was administered, the number of IFN-γ secreting cells significantly decreased by neutrophil depletion (FIG. 11, lower right).

Figure 12:
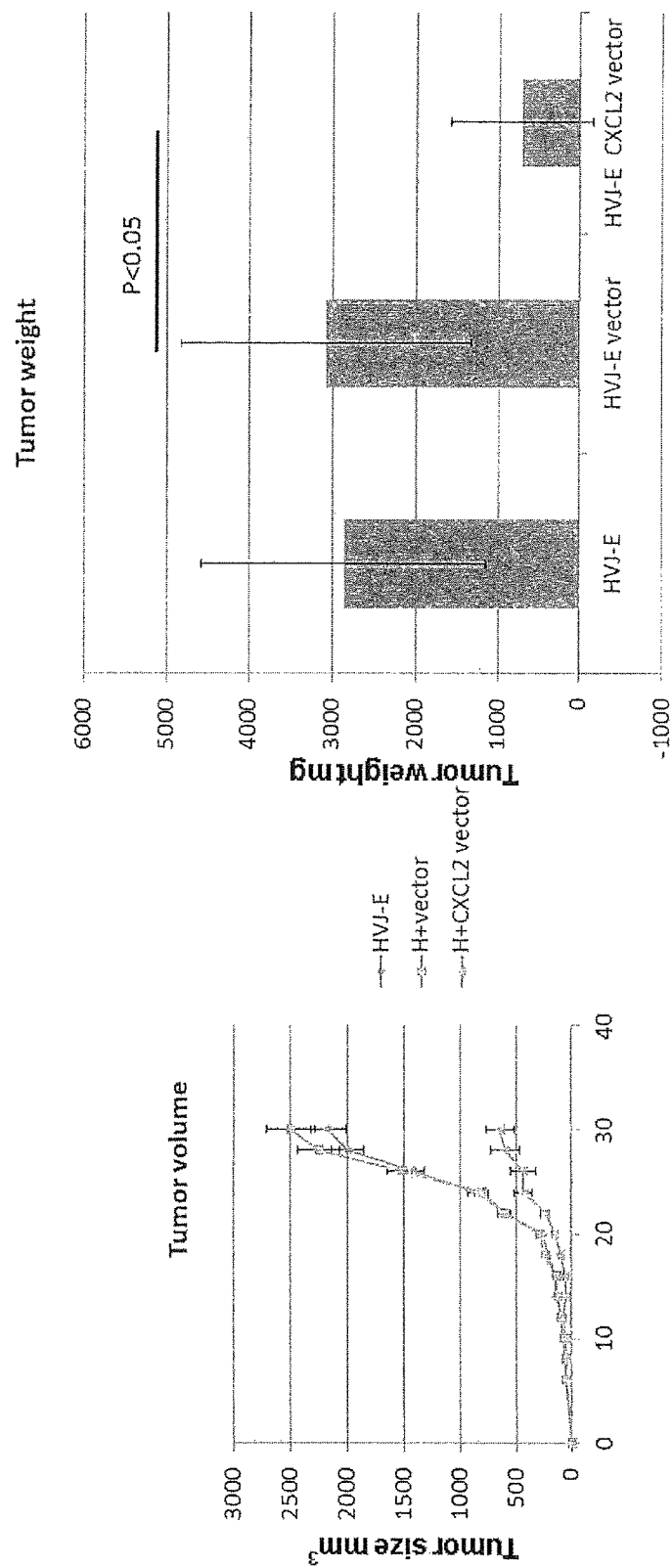
FIG. 12 shows tumor volume and tumor weight when HVJ-E, HVJ-E+pCY4B (H+vector) or HVJ-E+pCY4B-CXCL2 (H+CXCL2 vector) was administered.

Example 11 Antitumor Effect of Concomitant Drug of HVJ-E and CXCL2 Gene Expression Vector HVJ-E, HVJ-E+pCY4B or HVJ-E+pCY4B-CXCL2 was intratumorally injected to mouse melanoma cell line B16-F10-bearing C57BL/6N mice every two days 3 times in total, and the tumor size was observed. The results are shown in FIG. 12. Administration of HVJ-E+pCY4B-CXCL2 showed a higher effect in suppressing tumor proliferation in vivo as compared to that of HVJ-E+pCY4B.

Figure 13:
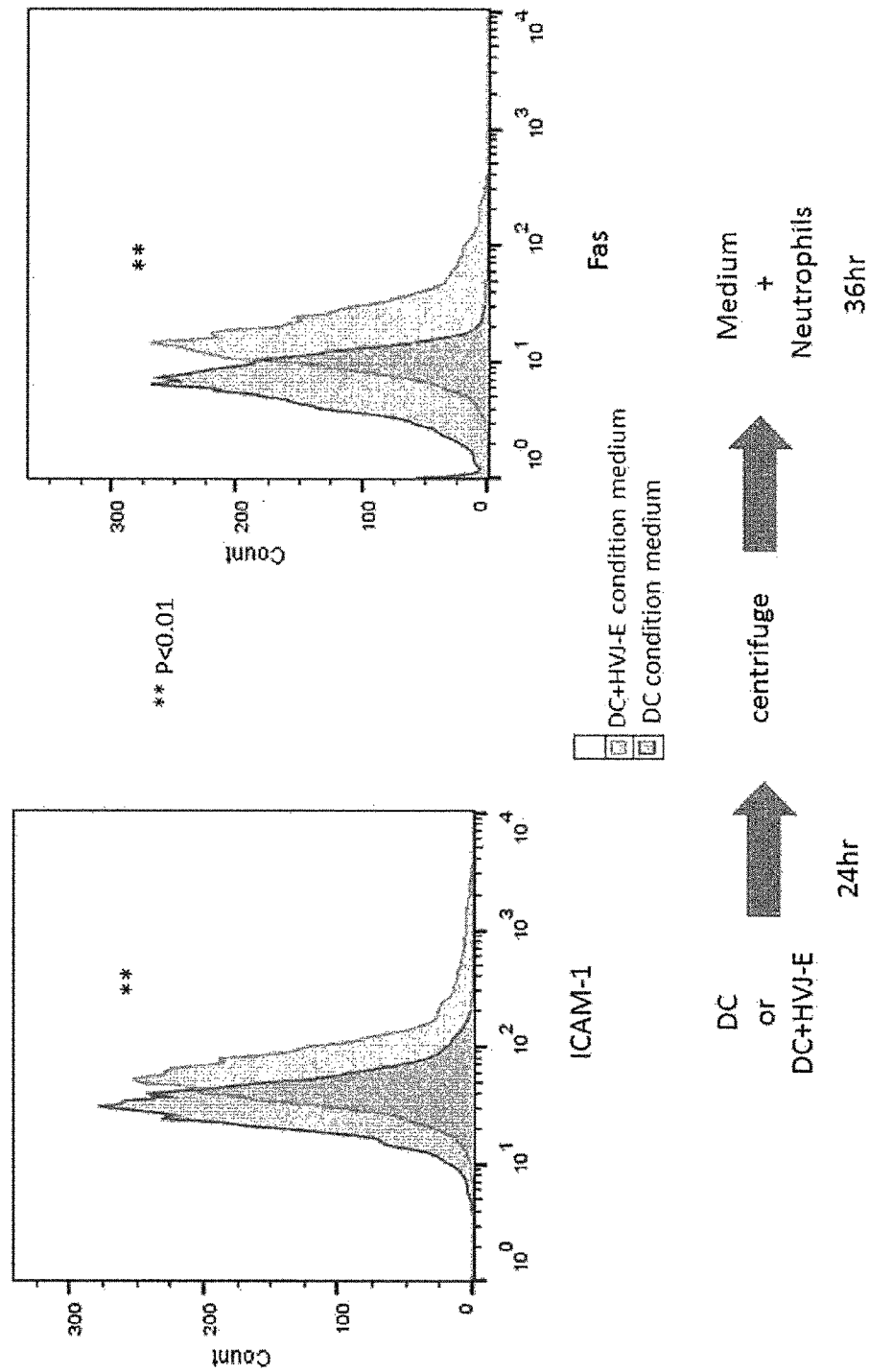
FIG. 13 shows results of analysis on the expression levels of ICAM-1 and Fas by a flow cytometry method when neutrophil was incubated in the culture supernatant of dendritic cells (DC) cultured with PBS or HVJ-E.

Example 12 Conversion of Neutrophil to N1 Type Neutrophil by HVJ-E Via Dendritic Cell Neutrophil was cultured using the culture supernatant of dendritic cell (DC) cultured together with HVJ-E, and induction of conversion of neutrophil to N1 type neutrophil was examined. $2 \times 10^8$ dendritic cells prepared from the mouse bone marrow were cultured with HVJ-E (500 m.o.i.) for 24 hr, and the conditioned medium (5 ml) thereof was centrifuged (18,500×g, 15 min, 4° C.) to remove the cells and HVJ-E. Neutrophil was cultured in the culture supernatant thereof for 36 hr, and the expressions of Fas and ICAM-1, which are N1 type neutrophil markers, were analyzed by flow cytometry (FACS). As a result, the culture supernatant of the dendritic cells cocultured with HVJ-E converted neutrophil to N1 type neutrophil (FIG. 13).

Figure 14:
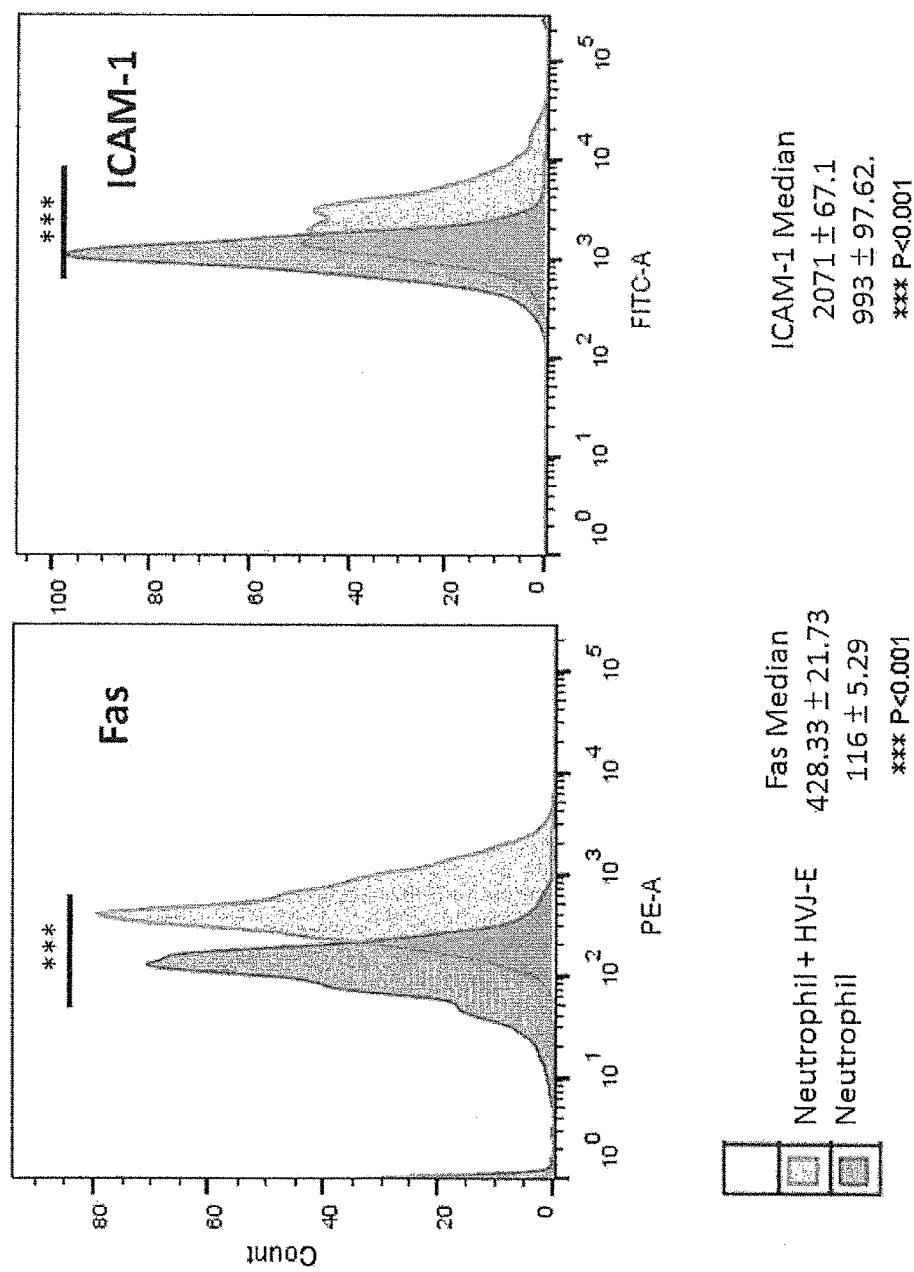
FIG. 14 shows results of analysis on the expression levels of ICAM-1 and Fas by a flow cytometry method when neutrophil was cultured together with PBS or HVJ-E.

Example 13 Conversion of Neutrophil to N1 Type Neutrophil by Direct Action of HVJ-E Whether HVJ-E directly acts on neutrophil to induce the conversion of neutrophil to N1 type neutrophil was examined. Neutrophil was separated by MACS with Neutrophil Isolation Kit (Miltenyi Biotec serial number 130-097-658) according to the use explanation of the Kit from the cells separated from the mouse bone marrow. After $2 \times 10^5$ neutrophils were seeded in a 96 well plate, HVJ-E was added at 500 m.o.i. and the expression of Fas and ICAM-1, which are N1 type neutrophil markers, was analyzed by flow cytometry (FACS) 24 hr later. As a result, the neutrophil cocultured with HVJ-E was converted to N1 type neutrophil (FIG. 14).

INDUSTRIAL APPLICABILITY

An anticancer agent containing HVJ-E (hemagglutinating virus of Japan envelope) and CXCL2, a nucleic acid comprising a base sequence encoding CXCL2 or a CXCL2 production inducing agent as active ingredients exhibits a lower dose than single use of each of them and a remarkable antitumor effect, and is useful as a novel therapeutic agent for cancer.

This application is based on a patent application No. 2015-164600 filed in Japan (filing date: Aug. 24, 2015), the contents of which are incorporated in full herein.

The invention claimed is:

1. A method for the prophylaxis or treatment of cancer, comprising administering an effective amount of a pharmaceutical composition comprising the following (1) and (2) to a subject:
   (1) HVJ-E (hemagglutinating virus of Japan envelope),
   (2) CXCL2 or a nucleic acid comprising a base sequence encoding CXCL2.

2. A method of inducing an N1 type neutrophil, comprising administering an effective amount a pharmaceutical composition comprising the following (1) and (2) to a subject:
   (1) HVJ-E (hemagglutinating virus of Japan envelope),
   (2) CXCL2 or a nucleic acid comprising a base sequence encoding CXCL2.

3. The method according to claim 1, wherein the cancer is selected from the group consisting of melanoma, lung cancer, mesothelioma, tongue cancer, esophagus cancer, gastric cancer, liver cancer, large intestine cancer, prostate cancer, kidney cancer, bladder cancer, breast cancer, uterine cancer, ovarian cancer, brain tumor, thyroid cancer, angiosarcoma, osteosarcoma, chondrosarcoma, rhabdomyosarcoma and leiomyosarcoma.

4. The method according to claim 1, wherein the nucleic acid comprising the base sequence encoding CXCL2 is an expression vector comprising a base sequence encoding CXCL2.

5. The method according to claim 4, wherein the cancer is selected from the group consisting of melanoma, lung cancer, mesothelioma, tongue cancer, esophagus cancer, gastric cancer, liver cancer, large intestine cancer, prostate cancer, kidney cancer, bladder cancer, breast cancer, uterine cancer, ovarian cancer, brain tumor, thyroid cancer, angiosarcoma, osteosarcoma, chondrosarcoma, rhabdomyosarcoma and leiomyosarcoma.

6. The method according to claim 4, wherein the nucleic acid comprising a base sequence encoding CXCL2 is encapsulated in HVJ-E.

7. The method according to claim 6, wherein the cancer is selected from the group consisting of melanoma, lung cancer, mesothelioma, tongue cancer, esophagus cancer, gastric cancer, liver cancer, large intestine cancer, prostate cancer, kidney cancer, bladder cancer, breast cancer, uterine cancer, ovarian cancer, brain tumor, thyroid cancer, angiosarcoma, osteosarcoma, chondrosarcoma, rhabdomyosarcoma and leiomyosarcoma.

8. The method according to claim 1, wherein the nucleic acid comprising a base sequence encoding CXCL2 is encapsulated in HVJ-E.

9. The method according to claim 8, wherein the cancer is selected from the group consisting of melanoma, lung cancer, mesothelioma, tongue cancer, esophagus cancer, gastric cancer, liver cancer, large intestine cancer, prostate cancer, kidney cancer, bladder cancer, breast cancer, uterine cancer, ovarian cancer, brain tumor, thyroid cancer, angiosarcoma, osteosarcoma, chondrosarcoma, rhabdomyosarcoma and leiomyosarcoma.

10. The method according to claim 2, wherein the nucleic acid comprising a base sequence encoding CXCL2 is an expression vector comprising a base sequence encoding CXCL2.

11. The method according to claim 10, wherein the nucleic acid comprising a base sequence encoding CXCL2 is encapsulated in HVJ-E.

12. The method according to claim 2, wherein the nucleic acid comprising a base sequence encoding CXCL2 is encapsulated in HVJ-E.

* * * * *